(12) United States Patent
Edwards

(10) Patent No.: US 11,154,283 B2
(45) Date of Patent: Oct. 26, 2021

(54) BODILY SEALANTS AND METHODS AND APPARATUS FOR IMAGE-GUIDED DELIVERY OF SAME

(71) Applicant: Veran Medical Technologies, Inc., St. Louis, MO (US)

(72) Inventor: Jerome R. Edwards, Nashville, TN (US)

(73) Assignee: Veran Medical Technologies, Inc., St. Louis, MO (US)

(*) Notice: Subject to any disclaimer, the term of this patent is extended or adjusted under 35 U.S.C. 154(b) by 263 days.

(21) Appl. No.: 16/052,745

(22) Filed: Aug. 2, 2018

(65) Prior Publication Data

US 2018/0338749 A1    Nov. 29, 2018

Related U.S. Application Data

(60) Division of application No. 13/405,290, filed on Feb. 25, 2012, now abandoned, which is a division of
(Continued)

(51) Int. Cl.
*A61B 8/12*  (2006.01)
*A61B 18/24*  (2006.01)
(Continued)

(52) U.S. Cl.
CPC ........ *A61B 17/00491* (2013.01); *A61B 5/062* (2013.01); *A61B 6/541* (2013.01);
(Continued)

(58) Field of Classification Search
CPC ...... A61B 17/00491; A61B 2034/2051; A61B 2034/2072; A61B 2090/3916;
(Continued)

(56) References Cited

U.S. PATENT DOCUMENTS

| 3,788,324 A | 1/1974 | Lim |
| 4,583,538 A | 4/1986 | Onik et al. |

(Continued)

FOREIGN PATENT DOCUMENTS

| DE | 19725137 | 1/1999 |
| DE | 19829224 | 1/2000 |

(Continued)

OTHER PUBLICATIONS

Dec. 22, 2016 USPTO Office Action (U.S. Appl. No. 14/989,671)—Our Matter 5734.

(Continued)

*Primary Examiner* — Patricia J Park
(74) *Attorney, Agent, or Firm* — Forsgren Fisher; James Urzedowski; Daniel Tysver

(57) ABSTRACT

Generally, systems, methods, and apparatus related to the use of a dynamic imaging modality in an image guided intervention are disclosed herein. More specifically, the use of such modalities in sealing a bodily opening, such as those that may be formed during an invasive medical procedure are disclosed herein. In some embodiments, a method includes viewing a representation of an instrument within a body of a patient, adjusting a position of the instrument based on the viewing such that a portion of the instrument is at a location within the body of the patient, and delivering a sealant via the instrument to the location within the body of the patient. The sealant is configured to seal an opening in the body part.

9 Claims, 15 Drawing Sheets

Related U.S. Application Data application No. 12/267,200, filed on Nov. 7, 2008, now Pat. No. 8,150,495, which is a continuation-in-part of application No. 12/146,738, filed on Jun. 26, 2008, now Pat. No. 7,853,307, which is a continuation of application No. 10/649,600, filed on Aug. 26, 2003, now Pat. No. 7,398,116.

(60) Provisional application No. 60/986,035, filed on Nov. 7, 2007, provisional application No. 60/494,268, filed on Aug. 11, 2003.

(51) Int. Cl.

| | | |
|---|---|---|
| *A61M 25/01* | (2006.01) | |
| *A61B 17/00* | (2006.01) | |
| *A61B 6/00* | (2006.01) | |
| *A61B 5/06* | (2006.01) | |
| *A61B 90/00* | (2016.01) | |
| *A61B 34/20* | (2016.01) | |
| *A61B 5/00* | (2006.01) | |
| *A61B 6/12* | (2006.01) | |
| *A61B 8/08* | (2006.01) | |
| *A61B 34/10* | (2016.01) | |
| *A61B 5/352* | (2021.01) | |

(52) U.S. Cl.
CPC .............. *A61B 34/20* (2016.02); *A61B 90/36* (2016.02); *A61B 5/352* (2021.01); *A61B 5/7285* (2013.01); *A61B 6/12* (2013.01); *A61B 8/0833* (2013.01); *A61B 34/10* (2016.02); *A61B 2017/00703* (2013.01); *A61B 2034/2051* (2016.02); *A61B 2034/2072* (2016.02); *A61B 2090/3916* (2016.02); *A61B 2090/3954* (2016.02); *A61B 2090/3958* (2016.02); *A61B 2090/3983* (2016.02)

(58) Field of Classification Search
CPC .... A61B 2090/3954; A61B 2090/3958; A61B 2090/3983; A61B 34/20; A61B 90/36; A61B 5/062; A61B 6/541; A61B 34/10
See application file for complete search history.

(56) References Cited

U.S. PATENT DOCUMENTS

| | | |
|---|---|---|
| 5,053,042 A | 10/1991 | Bidwell |
| 5,158,088 A | 10/1992 | Nelson et al. |
| 5,186,174 A | 2/1993 | Schlondorff et al. |
| 5,251,165 A | 10/1993 | James, III |
| 5,251,635 A | 10/1993 | Dumoulin et al. |
| 5,265,610 A | 11/1993 | Darrow et al. |
| 5,348,011 A | 9/1994 | Nessaiver |
| 5,377,678 A | 1/1995 | Dumoulin et al. |
| 5,391,199 A | 2/1995 | Ben-haim |
| 5,437,292 A | 8/1995 | Kipshidze et al. |
| 5,483,691 A | 1/1996 | Heck et al. |
| 5,483,961 A | 1/1996 | Kelly et al. |
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,718,241 A | 2/1998 | Ben-haim et al. |
| 5,730,129 A | 3/1998 | Darrow et al. |
| 5,740,808 A | 4/1998 | Panescu et al. |
| 5,765,561 A | 6/1998 | Chen et al. |
| 5,769,789 A | 6/1998 | Wang et al. |
| 5,769,861 A | 6/1998 | Vilsmeier |
| 5,771,306 A | 6/1998 | Stork et al. |
| 5,787,886 A | 8/1998 | Kelly et al. |
| 5,803,089 A | 9/1998 | Ferre et al. |
| 5,814,022 A | 9/1998 | Antanavich et al. |
| 5,814,066 A | 9/1998 | Spotnitz |
| 5,840,025 A | 11/1998 | Ben-haim |
| 5,868,673 A | 2/1999 | Vesely |
| 5,978,696 A | 11/1999 | Vomlehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa et al. |
| 6,122,541 A | 9/2000 | Cosman et al. |
| 6,132,396 A | 10/2000 | Antanavich et al. |
| 6,144,875 A | 11/2000 | Schweikard et al. |
| 6,167,296 A | 12/2000 | Shahidi |
| 6,173,201 B1 | 1/2001 | Front |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin et al. |
| 6,246,898 B1 | 6/2001 | Vesely et al. |
| 6,267,769 B1 | 7/2001 | Truwit |
| 6,275,560 B1 | 8/2001 | Blake et al. |
| 6,282,442 B1 | 8/2001 | Destefano et al. |
| 6,285,902 B1 | 9/2001 | Kienzle, III et al. |
| 6,298,259 B1 | 10/2001 | Kucharczyk et al. |
| 6,314,310 B1 | 11/2001 | Ben-haim et al. |
| 6,314,311 B1 | 11/2001 | Williams et al. |
| 6,314,312 B1 | 11/2001 | Wessels et al. |
| 6,317,616 B1 | 11/2001 | Glossop |
| 6,317,619 B1 | 11/2001 | Boernert et al. |
| 6,330,356 B1 | 12/2001 | Sundareswaran |
| 6,332,089 B1 | 12/2001 | Acker et al. |
| 6,332,891 B1 | 12/2001 | Himes |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson et al. |
| 6,368,331 B1 | 4/2002 | Front et al. |
| 6,369,571 B1 | 4/2002 | Damadian et al. |
| 6,379,302 B1 | 4/2002 | Kessman et al. |
| 6,381,485 B1 | 4/2002 | Hunter et al. |
| 6,402,762 B2 | 6/2002 | Hunter et al. |
| 6,418,238 B1 | 7/2002 | Shiratani et al. |
| 6,421,551 B1 | 7/2002 | Kuth et al. |
| 6,424,856 B1 | 7/2002 | Vilsmeier et al. |
| 6,425,865 B1 | 7/2002 | Salcudean et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen et al. |
| 6,468,265 B1 | 10/2002 | Evans et al. |
| 6,469,508 B1 | 10/2002 | Damadian et al. |
| 6,470,066 B2 | 10/2002 | Takagi et al. |
| 6,470,207 B1 | 10/2002 | Simon et al. |
| 6,473,635 B1 | 10/2002 | Rasche |
| 6,477,400 B1 | 11/2002 | Barrick |
| 6,478,793 B1 | 11/2002 | Cosman et al. |
| 6,478,802 B2 | 11/2002 | Kienzle, III et al. |
| 6,483,948 B1 | 11/2002 | Spink et al. |
| 6,484,049 B1 | 11/2002 | Seeley et al. |
| 6,485,413 B1 | 11/2002 | Boppart et al. |
| 6,490,467 B1 | 12/2002 | Bucholz et al. |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |

(56) References Cited

U.S. PATENT DOCUMENTS

| | | |
|---|---|---|
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,517,485 B2 | 2/2003 | Torp et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,562,059 B2 | 5/2003 | Edwards et al. |
| 6,567,687 B2 | 5/2003 | Front et al. |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,606,513 B2 | 8/2003 | Lardo et al. |
| 6,609,022 B2 | 8/2003 | Vilsmeier et al. |
| 6,636,757 B1 | 10/2003 | Jascob et al. |
| 6,650,924 B2 | 11/2003 | Kuth et al. |
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,772,002 B2 | 8/2004 | Schmidt et al. |
| 6,774,624 B2 | 8/2004 | Anderson et al. |
| 6,782,287 B2 | 8/2004 | Grzeszczuk et al. |
| 6,796,988 B2 | 9/2004 | Melkent et al. |
| 6,799,569 B2 | 10/2004 | Danielsson et al. |
| 6,823,207 B1 | 11/2004 | Jensen et al. |
| 6,826,423 B1 | 11/2004 | Hardy et al. |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,907,281 B2 | 6/2005 | Grzeszczuk |
| 6,920,347 B2 | 7/2005 | Simon et al. |
| 6,925,200 B2 | 8/2005 | Wood et al. |
| 6,934,575 B2 | 8/2005 | Ferre et al. |
| 6,968,224 B2 | 11/2005 | Kessman et al. |
| 6,978,166 B2 | 12/2005 | Foley et al. |
| 7,015,859 B2 | 3/2006 | Anderson |
| 7,015,907 B2 | 3/2006 | Tek et al. |
| 7,050,845 B2 | 5/2006 | Vilsmeier |
| 7,139,601 B2 | 11/2006 | Bucholz et al. |
| 7,153,297 B2 | 12/2006 | Peterson |
| 7,171,257 B2 | 1/2007 | Thomson |
| 7,174,201 B2 | 2/2007 | Govari et al. |
| 7,260,426 B2 | 8/2007 | Schweikard et al. |
| 7,366,562 B2 | 4/2008 | Dukesherer et al. |
| 7,398,116 B2 | 7/2008 | Edwards |
| 7,505,806 B2 | 3/2009 | Masutani et al. |
| 7,697,972 B2 | 4/2010 | Verard et al. |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Thomas, III et al. |
| 2001/0041835 A1 | 11/2001 | Front et al. |
| 2002/0044631 A1 | 4/2002 | Graumann et al. |
| 2002/0049375 A1 | 4/2002 | Strommer et al. |
| 2002/0049378 A1 | 4/2002 | Grzeszczuk et al. |
| 2002/0070970 A1 | 6/2002 | Wood et al. |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk et al. |
| 2002/0085681 A1 | 7/2002 | Jensen |
| 2002/0143317 A1 | 10/2002 | Glossop |
| 2002/0161295 A1 | 10/2002 | Edwards et al. |
| 2003/0000535 A1 | 1/2003 | Robert, Jr. et al. |
| 2003/0004411 A1 | 1/2003 | Govari et al. |
| 2003/0016852 A1 | 1/2003 | Kaufman et al. |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0029464 A1 | 2/2003 | Chen et al. |
| 2003/0032878 A1 | 2/2003 | Shahidi |
| 2003/0040667 A1 | 2/2003 | Feussner et al. |
| 2003/0074011 A1 | 4/2003 | Gilboa et al. |
| 2003/0088179 A1 | 5/2003 | Seeley et al. |
| 2003/0120339 A1* | 6/2003 | Banik ............... A61L 31/16 623/1.42 |
| 2003/0125622 A1 | 7/2003 | Schweikard et al. |
| 2003/0130576 A1 | 7/2003 | Seeley et al. |
| 2003/0139663 A1 | 7/2003 | Graumann |
| 2003/0199785 A1 | 10/2003 | Hibner et al. |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0018228 A1* | 1/2004 | Fischell ............ A61K 9/127 424/450 |
| 2004/0034300 A1 | 2/2004 | Verard et al. |
| 2004/0049121 A1 | 3/2004 | Yaron |
| 2004/0076259 A1 | 4/2004 | Jensen et al. |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jascob et al. |
| 2004/0122311 A1 | 6/2004 | Cosman |
| 2004/0138548 A1 | 7/2004 | Strommer et al. |
| 2004/0138562 A1* | 7/2004 | Makower ............ A61B 6/12 600/439 |
| 2004/0147837 A1* | 7/2004 | Macaulay ........... A61B 34/20 600/424 |
| 2004/0147901 A1* | 7/2004 | Py .................. A61M 5/2033 604/506 |
| 2004/0152970 A1 | 8/2004 | Hunter et al. |
| 2004/0152974 A1 | 8/2004 | Solomon |
| 2004/0167393 A1 | 8/2004 | Solar et al. |
| 2004/0193042 A1 | 9/2004 | Scampini et al. |
| 2004/0210125 A1 | 10/2004 | Chen et al. |
| 2005/0010099 A1 | 1/2005 | Raabe et al. |
| 2005/0027186 A1 | 2/2005 | Chen et al. |
| 2005/0033149 A1 | 2/2005 | Strommer et al. |
| 2005/0038337 A1 | 2/2005 | Edwards |
| 2005/0065433 A1 | 3/2005 | Anderson |
| 2005/0085793 A1 | 4/2005 | Glossop |
| 2005/0107688 A1 | 5/2005 | Strommer |
| 2005/0113809 A1 | 5/2005 | Melkent et al. |
| 2005/0143651 A1 | 6/2005 | Verard et al. |
| 2005/0169510 A1 | 8/2005 | Zuhars et al. |
| 2005/0182319 A1 | 8/2005 | Glossop |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1 | 1/2006 | Saracen |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0058737 A1* | 3/2006 | Herweck ............ A61M 25/00 604/164.01 |
| 2006/0063998 A1 | 3/2006 | Von Jako et al. |
| 2006/0064006 A1 | 3/2006 | Strommer et al. |

(56) References Cited

U.S. PATENT DOCUMENTS

| | | |
|---|---|---|
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0142798 A1 | 6/2006 | Holman et al. |
| 2006/0173269 A1 | 8/2006 | Glossop |
| 2006/0173291 A1 | 8/2006 | Glossop |
| 2006/0189867 A1 | 8/2006 | Revie et al. |
| 2006/0247511 A1 | 11/2006 | Anderson |
| 2007/0032723 A1 | 2/2007 | Glossop |
| 2007/0038058 A1 | 2/2007 | West et al. |
| 2007/0055142 A1 | 3/2007 | Webler |
| 2007/0066887 A1 | 3/2007 | Mire et al. |
| 2007/0110289 A1 | 5/2007 | Fu et al. |
| 2007/0129629 A1 | 6/2007 | Beauregard et al. |
| 2007/0167744 A1 | 7/2007 | Beauregard et al. |
| 2008/0140114 A1 | 6/2008 | Edwards et al. |
| 2012/0158047 A1 | 6/2012 | Edwards et al. |

FOREIGN PATENT DOCUMENTS

| | | |
|---|---|---|
| DE | 19909816 | 5/2000 |
| DE | 10136709 | 2/2003 |
| DE | 10161160 | 6/2003 |
| DE | 102005010010 | 9/2005 |
| DE | 102004030836 | 1/2006 |
| DE | 102005038394 | 3/2006 |
| DE | 102005050286 | 4/2006 |
| DE | 102004058122 | 7/2006 |
| EP | 0501993 | 9/1992 |
| EP | 0869745 | 10/1998 |
| EP | 0900048 | 2/2000 |
| EP | 0977510 | 2/2000 |
| EP | 1079240 | 2/2001 |
| EP | 1152706 | 11/2001 |
| EP | 1181897 | 2/2002 |
| EP | 1319368 | 6/2003 |
| EP | 1374792 | 1/2004 |
| EP | 1374793 | 1/2004 |
| EP | 1391181 | 2/2004 |
| EP | 1421913 | 5/2004 |
| EP | 1464285 | 10/2004 |
| EP | 1504713 | 2/2005 |
| EP | 1504726 | 2/2005 |
| EP | 1519140 | 3/2005 |
| EP | 1523951 | 4/2005 |
| EP | 1561423 | 8/2005 |
| EP | 1629774 | 3/2006 |
| EP | 1629789 | 3/2006 |
| FR | 2876273 | 4/2006 |
| WO | 9501757 | 1/1995 |
| WO | 9608209 | 3/1996 |
| WO | 9610949 | 4/1996 |
| WO | 9729699 | 8/1997 |
| WO | 9729709 | 8/1997 |
| WO | 9836684 | 8/1998 |
| WO | 9916352 | 4/1999 |
| WO | 9943253 | 9/1999 |
| WO | 0028911 | 5/2000 |
| WO | 0047103 | 8/2000 |
| WO | 0049958 | 8/2000 |
| WO | 0057767 | 10/2000 |
| WO | 0069335 | 11/2000 |
| WO | 0101845 | 1/2001 |
| WO | 0137748 | 5/2001 |
| WO | 0162134 | 8/2001 |
| WO | 0164124 | 9/2001 |
| WO | 0176496 | 10/2001 |
| WO | 0176497 | 10/2001 |
| WO | 0187136 | 11/2001 |
| WO | 0193745 | 12/2001 |
| WO | 0200093 | 1/2002 |
| WO | 0200103 | 1/2002 |
| WO | 0219936 | 3/2002 |
| WO | 0222015 | 3/2002 |
| WO | 0224051 | 3/2002 |
| WO | 02056770 | 7/2002 |
| WO | 02064011 | 8/2002 |
| WO | 02082375 | 10/2002 |
| WO | 02098273 | 12/2002 |
| WO | 04046754 | 6/2004 |
| WO | 04060157 | 7/2004 |
| WO | 04062497 | 7/2004 |
| WO | 05070318 | 8/2005 |
| WO | 05077293 | 10/2005 |
| WO | 05101277 | 10/2005 |
| WO | 05111942 | 11/2005 |
| WO | 06002396 | 1/2006 |
| WO | 06005021 | 1/2006 |
| WO | 06027781 | 3/2006 |
| WO | 06039009 | 4/2006 |
| WO | 06051523 | 5/2006 |
| WO | 06090141 | 8/2006 |
| WO | 07002079 | 1/2007 |
| WO | 07031314 | 3/2007 |
| WO | 07033206 | 3/2007 |
| WO | 07062051 | 5/2007 |
| WO | 07084893 | 7/2007 |

OTHER PUBLICATIONS

Mar. 9, 2016 USPTO Office Action (U.S. Appl. No. 14/989,671)—Our Matter 5734.
May 15, 2018 USPTO Office Action (U.S. Appl. No. 14/989,671)—Our Matter 5734.
Jul. 14, 2017 USPTO Office Action (U.S. Appl. No. 14/989,671)—Our Matter 5734.
Educational Highlights from Data Presented at the 5th Joint Meeting of the EU Association for Cardio-Thoracic Surgery (EACTS) and the EU Society of Thoracic Surgeons (ESTS).
"Evidence for Fleece-Bound Sealants in Cardiothoracic Surgery" Sep. 9-13, 2006, 4 pages.
FDA Approves Lung Sealant, May 31, 2000 [online] [Retrieved on Oct. 17, 2008] Retrieved from the Internet <URL: http://www.meds.com/archive/mol-cancer/2000/05/msg01329.html.
Medical Industry Today, "New Navigational Aid Could Improve Hip Replacement Outcomes," Jul. 22, 1997.
Moore, E. et al. "Needle Aspiration Lung Biopsy: Reevaluation of the Blood Patch Technique in an Equine Model", Radiology, vol. 196, No. Jul. 1, 1995, pp. 183-186.

* cited by examiner

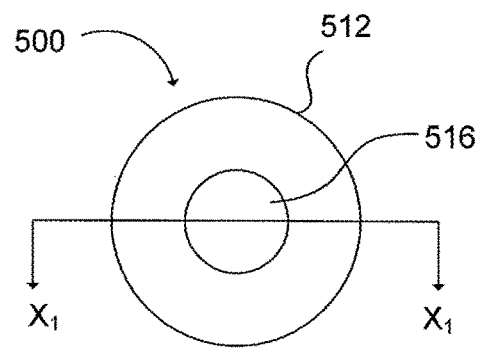
FIG. 12
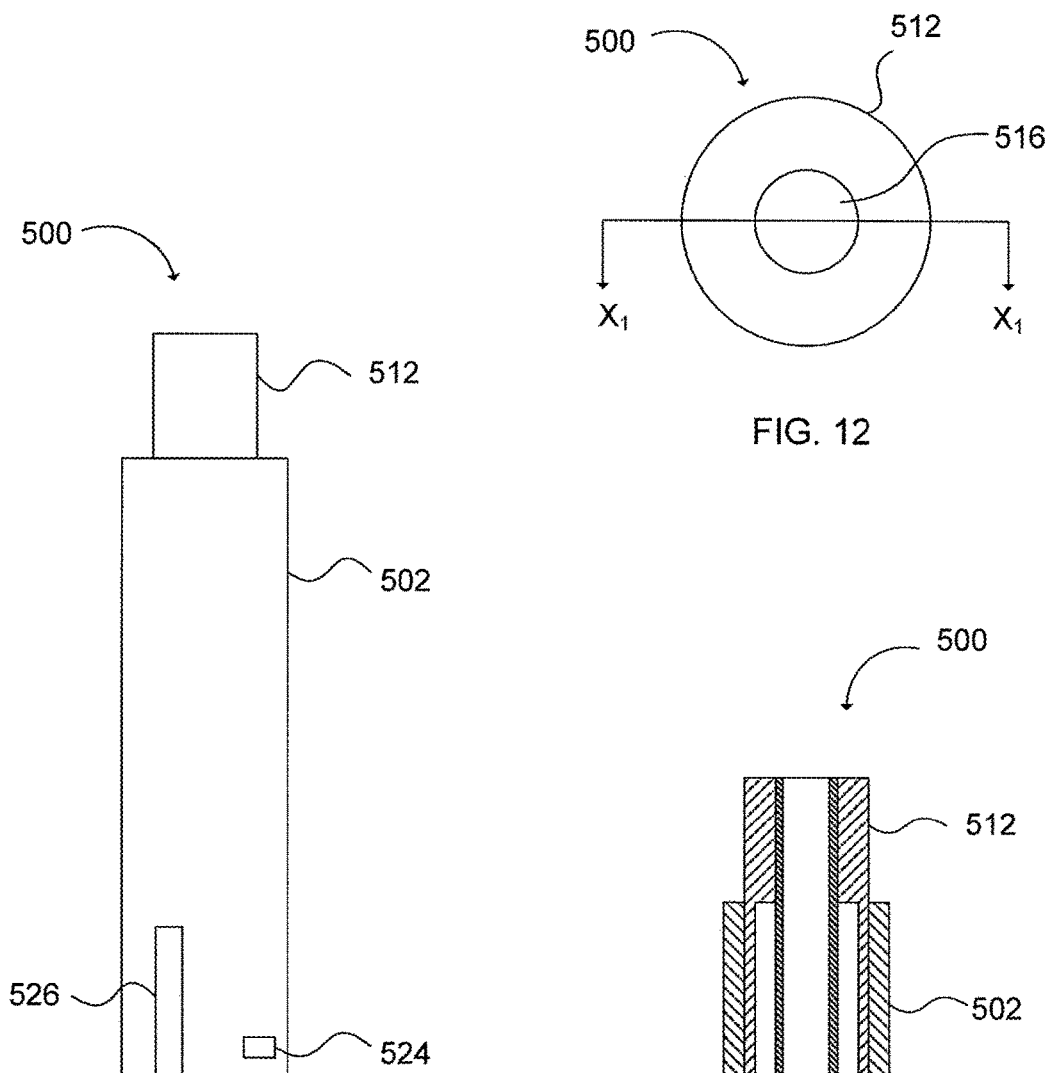
FIG. 11
FIG. 13

BODILY SEALANTS AND METHODS AND APPARATUS FOR IMAGE-GUIDED DELIVERY OF SAME

CROSS-REFERENCE TO RELATED APPLICATIONS

This application is a divisional of U.S. patent application Ser. No. 13/405,290 filed on Feb. 25, 2012, which is a divisional application of, and claims priority to, U.S. patent application Ser. No. 12/267,200 filed on Nov. 7, 2008, entitled "Bodily Sealants and Methods and Apparatus for Image-Guided Delivery of Same," which claims priority to and is a continuation-in-part of U.S. patent application Ser. No. 12/146,738, filed on Jun. 26, 2008, entitled "Methods, Apparatuses, and Systems Useful in Conducting Image Guided Interventions," which claims priority to and is a continuation of U.S. Pat. No. 7,398,116, filed on Aug. 26, 2003, entitled, "Methods, Apparatuses, and Systems Useful in Conducting Image Guided Interventions," which claims priority to U.S. Provisional Patent Application Ser. No. 60/494,268, filed Aug. 11, 2003, entitled "Methods, Apparatuses, and Systems Useful in Conducting Image Guided Interventions," the entire contents of each are hereby incorporated by reference.

BACKGROUND

Image guided surgery, also known as image guided intervention (IGI), is used to enhance a physician's understanding of the location of a medical instrument within a patient's body during a medical procedure. Some known IGI applications include the use of 2-dimensional (2-D) and 3-dimensional (3-D) imaging modalities. The usefulness of known techniques, however, is limited to procedures involving relatively static anatomy. In other words, the usefulness of known techniques is generally limited to use with respect to anatomy that exhibits no or minimal movement with respect to cardiac and/or respiratory cycles.

Image guided surgery, also known as image guided intervention (IGI), is used to enhance a physician's understanding of the location of a medical instrument within a patient's body during a medical procedure. Some known IGI applications include the use of 2-dimensional (2-D) and 3-dimensional (3-D) imaging modalities. The usefulness of known techniques, however, is limited to procedures involving relatively static anatomy. In other words, the usefulness of known techniques is generally limited to use with respect to anatomy that exhibits no or minimal movement with respect to cardiac and/or respiratory cycles.

Thus, known IGI techniques have limited application, if any, in medical procedures involving dynamic anatomy (i.e., anatomy that exhibits more than minimal movement with respect to cardiac and respiratory cycles).

Moreover, known IGI systems fail to account for imaging data that includes an irregular pattern exhibited by a patient, such as an irregular pattern resulting from the application of a medical therapy to the patient. For example, in certain instances, a patient may have an irregular ECG waveform pattern as a result of implantation of a pacemaker and/or a cardioverter defibrillator lead. In another example, a patient may have an irregular ECG waveform pattern as a result of radiofrequency ablation of myocytes to cure tachycardia.

Known IGI systems can use an external reference probe to calculate a transformation between a spatial coordinate system (e.g., in the patient space) and an image coordinate system (e.g., in the image space as acquired by the imaging modality). In certain instances, such known external probes can fail to produce a desired transformation accuracy due to a moment arm escalation of error. In other words, in certain circumstances, the accuracy of the transformation of known IGI systems can be adversely affected by the distance between the target anatomy and the external probe. Although some IGI systems include a reference probe configured to be inserted into the body, such known reference probes are positioned on a proximal end portion of the instrument, and thus fail to remedy the moment arm escalation of error.

Use of known instruments in a medical procedure can result in the penetration, incising, puncturing, or otherwise accessing a portion of the patient's anatomy. Such procedures, however, can result in many harmful side effects. For example, in a procedure involving access to the patient's lung, the lung may collapse and/or pneumothorax may occur when the chest wall is punctured. Furthermore, foreign substances may enter the patient's body and/or a portion of the patient's anatomy through the site of entry.

Thus, a need exists for improved apparatus and methods for sealing an opening (e.g., a site of entry) within a patient's body. Moreover, a need exists for improved methods for using image guided surgery to seal such an opening.

SUMMARY

Generally, systems, methods, and apparatus related to the use of a dynamic imaging modality in an image guided intervention are disclosed herein. More specifically, the use of such modalities in sealing a bodily opening, such as those that may be formed during an invasive medical procedure are disclosed herein. In some embodiments, a method includes viewing a representation of an instrument within a body of a patient, adjusting a position of the instrument based on the viewing such that a portion of the instrument is at a location within the body of the patient, and delivering a sealant via the instrument to the location within the body of the patient. The sealant is configured to seal an opening in the body part.

BRIEF DESCRIPTION OF THE DRAWINGS

FIG. 11 is a front view of an apparatus according to an embodiment.

FIG. 12 is a top view of the apparatus of FIG. 11.

FIG. 13 is a cross-sectional view of the apparatus of FIG. 11 taken along line X.sub.1-X.sub.1 of FIG. 12.

DETAILED DESCRIPTION

Figure 1:
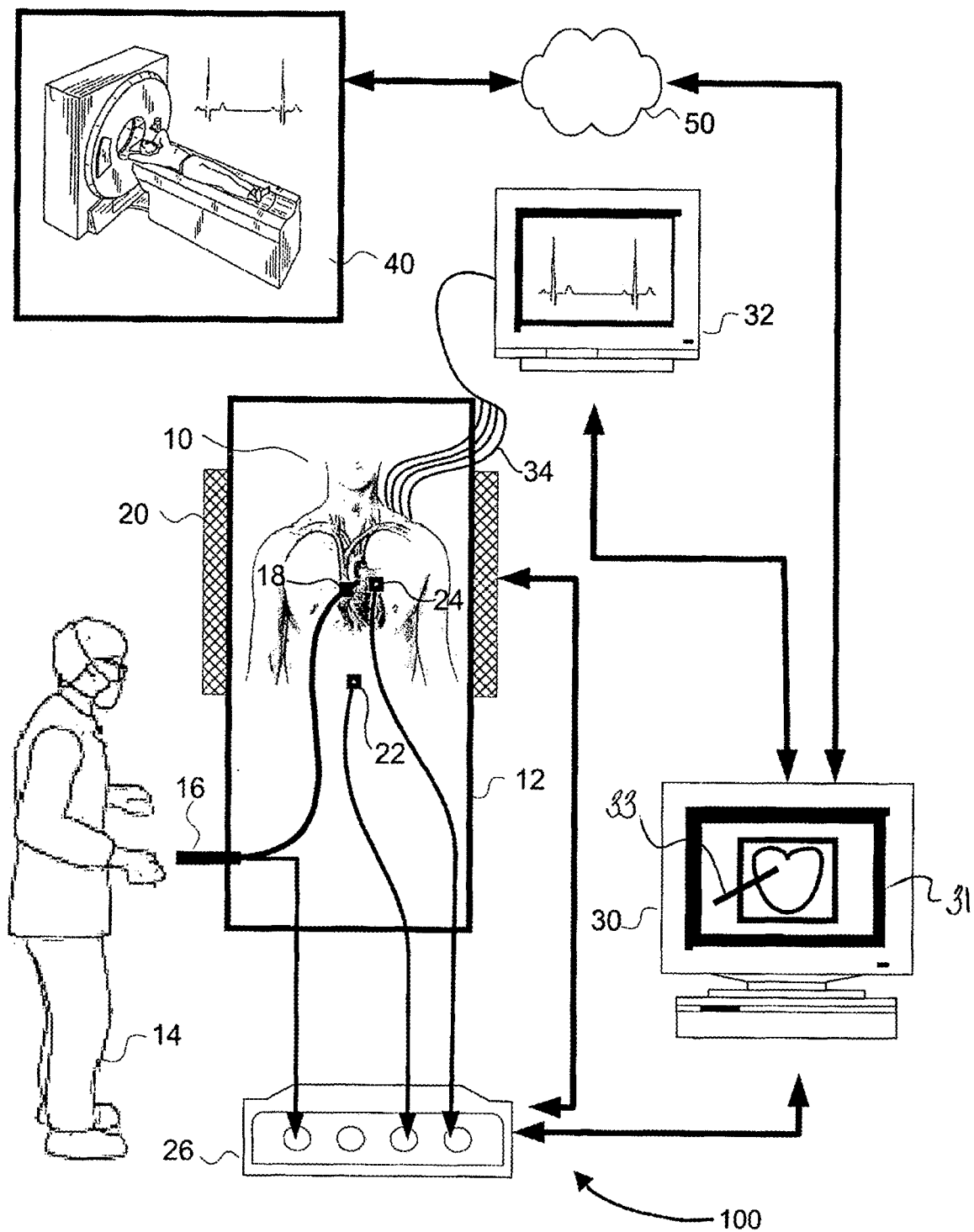
FIG. 1 is a schematic illustration of a system according to an embodiment, and a physician and a patient.

Generally, apparatus and methods directed to enabling the use of dynamic imaging modalities in a 2-dimensional (2-D), 3-dimensional (3-D), and/or 4-dimensional (4-D) image guided intervention (IGI), and specifically to use of such modalities in sealing a bodily opening, such as those that may be formed during an invasive medical procedure, are described herein. Also disclosed herein are apparatus and methods for sealing such a bodily opening in the patient, and specifically to apparatus and methods for sealing such an opening in a dynamic bodily tissue.

In some embodiments, for example, a system is configured for use with respect to a target dynamic anatomy, or anatomy that exhibits more than minimal movement with respect to a patient's cardiac and/or respiratory cycle (e.g., with respect to the patient's heartbeat and/or breathing). Examples of such target anatomy include the heart, lungs, kidneys, liver, and/or blood vessels. The system can be configured to synchronize positional information associated with a location of at least one reference marker disposed proximate to the body of the patient with at least one image that represents the target anatomy of the patient when the target anatomy is in a particular orientation and/or configuration. In some embodiments, the system is configured to select an image that represents the target anatomy at a specified time (e.g., a time at which expiration of air from the lungs is occurring). The system is configured to superimpose a representation of a medical instrument on the image after making a transformation of the instrument from a tracking space (e.g., an area proximate to the patient's body, or a real coordinate space) to an image space (e.g., a computer-assisted representation of the image of the target anatomy).

In another example, a method according to an embodiment includes selecting an image from a set of images depicting a target dynamic anatomy such that the selected image is associated with a current position and/or orientation of the target dynamic anatomy in an operating theatre (e.g., a medical facility, a doctor's office, or an operating room). The method can include synchronizing a location of a reference marker that is proximate to the body of the patient (in the form of a vector, for example) to each image in the set of images. The method can also include calculating a transformation between a tracking space and an image space using the positional information of the marker in order to superimpose a live (or current) position of a medical instrument onto a display of the image.

In yet another example, a method of delivering a sealant using a dynamic imaging modality includes viewing a representation of an instrument disposed within a body of a patient. The representation of the instrument is superimposed on an image from a set of images associated with a cyclical movement of a body part. The image is associated with a match dataset vector (MDV). The MDV is a dataset vector associated with a current vector that is calculated based on a current position of a first reference marker and a current position of a second reference marker. The second reference marker is depicted in at least one image from the set of images. The method includes adjusting a position of the instrument based on the viewing such that a portion of the instrument is at a location within the body of the patient. The location can be, for example, adjacent a surface of a body part (e.g., the heart, the lung, etc.) The method includes delivering a sealant via the instrument to the location within the body of the patient. The sealant is configured to seal an opening in the body part.

In some embodiments, for example, an apparatus includes a first shaft and a second shaft. The first shaft defines a lumen and an opening in communication with the lumen of the first shaft. At least a portion of the first shaft is disposable within a body of a patient. The second shaft defines a chamber and an opening in communication with the chamber of the second shaft. The chamber of the second shaft is configured to receive a sealant. The second shaft is configured to be movably received within the lumen of the first shaft. The second shaft has a first position in which the opening of the second shaft is fluidically isolated from the opening of the first shaft and a second position in which the opening of the second shaft is in fluid communication with the opening of the first shaft. The opening of the first shaft and the opening of the second shaft define a flow passageway for the sealant when the second shaft is in its second position.

In some embodiments, an apparatus includes an elongate shaft and a delivery mechanism. The elongate shaft has a proximal end portion and a distal end portion. The elongate shaft defines a lumen. At least a portion of the elongate shaft is disposable within a body of a patient. The delivery mechanism is movably coupled to the elongate shaft. The delivery mechanism is configured to move a seal member configured to seal an opening within the body of the patient between a collapsed configuration and an expanded configuration. At least a portion of the seal member is disposed within the lumen of the elongate shaft when the seal member is in the collapsed configuration. The seal member is configured to be disposed in the body of the patient apart from the elongate shaft and the delivery mechanism.

In some embodiments, an apparatus includes an elongate member that defines a lumen. At least a portion of the elongate member is configured to define an opening within a bodily tissue. A coating is disposed on at least a portion of an outer surface of the elongate member. The coating is configured to form a seal between the elongate member and the bodily tissue when the portion of the elongate member is within the opening of the bodily tissue.

In some embodiments, an apparatus includes a substrate and a sealant. The substrate has a first surface and a second surface different than the first surface. The substrate is couplable to a dynamic bodily tissue within a bodily cavity of a patient. The substrate is penetrable by a medical instrument. The sealant is disposed on a portion of the substrate. The sealant is penetrable by the medical instrument. The sealant is configured to substantially prevent passage of a material through an opening in the substrate formed by the medical instrument.

FIG. 1 is an illustration of a system 100 according to an embodiment. The system 100 can be configured to perform segmentation, correlation and registration between data obtained in "image space" (position data taken pre-procedurally) and data obtained in "tracking space" (position data obtained during a later medical procedure), as described herein and as described in detail in U.S. Patent Publication No. 2007/0060799, filed Apr. 25, 2006, entitled, "Apparatus and Method for Automatic Image Guided Accuracy Verification," (the "'799 application") the entire contents of which is hereby incorporated by reference.

The system 100 includes an imaging device 40, a processor 30, reference markers 18, 22, 24, a tracker 20, a converter 26, and a monitor 32. The system 100 is configured to facilitate the performance of an IGI by a physician 14 on a patient 10. The IGI system 100 can be utilized for a variety of medical purposes, including, but not limited to, pacemaker lead placement, coronary stent placement, cardiac radiofrequency ablation, lung biopsy, renal stent placement, transjugular intrahepatic porto-systemic shunting, and/or percutaneous radio frequency ablation of renal masses, among other procedures. Moreover, the IGI system 100 can be used to deliver a seal member (e.g., a patch) and/or a sealant to a body part during such procedures.

The imaging device 40 (also referred to herein as the imaging modality or scanner) is coupled to the processor 30. In some embodiments, for example, the imaging device 40 is electronically coupled to the processor 30 via a network 50 (e.g., a hospital network). The network 50 may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

The imaging device 40 is configured to take, acquire, capture, and/or generate an image of at least a portion of the body of the patient 10, such as a portion including a target anatomy. The target anatomy can be an internal dynamic anatomy, such as the heart, lung, blood vessel, or the like. In some embodiments, the imaging device 40 is configured to take a series of images of the target anatomy. For example, in some embodiments, the imaging device 40 is configured to take a set of images of the same portion of the target anatomy where each image from the set of images is taken at a different time. In other words, the imaging device 40 is configured to take a first image of the target anatomy from a first perspective at a first time, and a second image of the target anatomy from the first perspective at a second later time. In some embodiments, the imaging device 40 is configured to concurrently take a set of images of the target anatomy with each image being taken from a perspective different than the perspective of the other images being taken. In this manner, the series of images can be used to generate a multi-dimensional representation of the target anatomy.

The imaging device 40 can be configured to take, acquire, capture, and/or generate the images pre-operatively, post-operatively, and/or during the operation. In some procedures, the images are taken pre-operatively to facilitate the performance of the procedure using IGI. The imaging device 40 can be configured to take an image of the body of the patient along more than one plane. The imaging device 40 can be any suitable 2-D, 3-D, or 4-D imaging modality. For example, in some embodiments, the imaging device 40 can be configured as a single-head C-arm fluoroscope (not shown) configured to take a virtual bi-plane image by rotating the C-arm about at least two planes, which could be orthogonal planes to generate two-dimensional images that can be converted to three-dimensional volumetric images.

The images can be displayed as 2-D, 3-D, and/or 4-D representations by the system 100, such as, for example, on a graphical user interface (GUI) 31 of the processor 30 or other portion of the system 100. In this manner, and as described in more detail herein, by acquiring and/or displaying images in more than one plane, an icon representing the location of a medical instrument 16 within the body of the patient 10 can be superimposed on at least one multi-dimensional image when the image is displayed to the physician 14. For example, in some embodiments, a 4-D surface rendering of the target anatomy can be achieved by incorporating patient data or other data from an atlas or anatomical model map, or from pre-operative image data captured by the imaging device 40.

The imaging device 40 can be an imaging device configured for any suitable imaging modality, such as isocentric fluoroscopy, bi-plane fluoroscopy, cinematography (CINE) fluoroscopy ultrasound, high frequency ultrasound (HIFU), intra-vascular ultrasound (IVUS), computed tomography (CT), optical coherence tomography (OCT), multi-slice computed tomography (MSCT), magnetic resonance imaging (MRI), single photon emission computer tomography (SPECT), and/or positron emission tomography (PET), or any combination thereof.

For example, MRI is generally performed pre-operatively using a non-ionizing field. MRI can provide a desired quality of tissue visualization in 3-D form and can provide anatomical and functional information from the imaging. MRI data can be registered and compensated for motion correction using a reference marker, as described in more detail herein. PET is generally a pre-operative imaging procedure that can expose the patient to some level of radiation to provide a 3-D image. PET data can provide functional information and also can be registered and compensated for motion correction using a reference marker. CT is also generally a pre-operative technique that exposes the patient to a limited level of radiation. CT can be a very fast imaging procedure, at least as compared to imaging procedures using a different type of imaging device. A multi-slice CT system can provide a set of 3-D images having a desired quality of resolution and anatomical information. CT imaging data generally can be registered and compensated for motion correction using a reference marker.

Fluoroscopy is generally an intra-operative imaging procedure that can expose the patient to a certain amount of radiation and that can provide 2-D and/or rotational 3-D images. Fluoroscopic images generally provide a desired quality of resolution and anatomical information. Fluoroscopic images can be either manually or automatically registered and can also be compensated for motion correction using a reference marker. Ultrasound imaging is also generally an intra-operative procedure which uses a non-ionizing field to provide either 2-D, 3-D, or 4-D imaging, including anatomical and/or blood flow information. Ultrasound imaging provides automatic registration and does not need to account for any motion correction. Such imaging modalities are also described in U.S. Patent Publication No. 2006/0025677, filed Jul. 11, 2005, entitled, "Method and Apparatus for Surgical Navigation," the entire contents of which is hereby incorporated by reference.

In some embodiments, the imaging device 40 includes a hybrid imaging modality. For example, the imaging device 40 can be a hybrid of PET and CT. In another example, the imaging device 40 can be a hybrid of SPECT and CT. The hybrid imaging modality can provide functional image data superimposed onto anatomical data to be used to navigate to and/or localize target anatomy within the patient 10, as described in more detail herein.

In some embodiments, the imaging device 40 can be a gated imaging device, such as, for example, an electrocardiogram-gated (ECG-gated) magnetic resonance imaging (MRI) device and/or an ECG-gated computed tomography (CT) device. As illustrated in FIG. 1, the monitor 32 (e.g., an ECG monitor) can be attached to the patient 10 via a set of leads 34 and/or electrodes (not shown). The monitor 32 and the imaging device 40 are each in electrical communication with the processor 30. In this manner, the imaging device 40 is gated based on information received by the processor from the monitor 32, as described in detail herein. Some bodily functions, e.g., respiration and circulation, can cause movement of the target anatomy relative to the medical instrument 16, even when the medical instrument 16 has not been moved by the physician and/or relative to a static reference point external to the body of the patient (e.g., a table 12). Therefore, the imaging device 40 can be configured to acquire the image(s) on a time-gated basis triggered by a physiological (or physiologically-related) signal. For example, the physiological signal can be an ECG signal acquired via the leads 34 (or from a sensing electrode included on the medical instrument 16 or from a separate reference probe). A characteristic of this signal, such as an R-wave peak or P-wave peak associated with ventricular or atrial depolarization, respectively, may be used to trigger the gate image acquisition with the imaging device 40.

Figure 2:
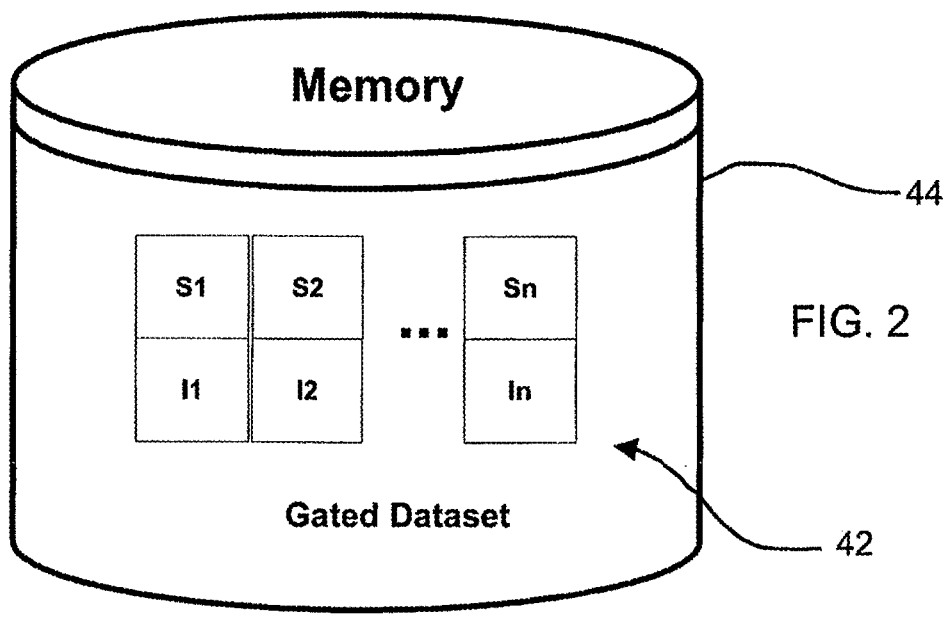
FIG. 2 is a schematic illustration of a dataset according to an embodiment stored in a portion of the system of FIG. 1.
Figure 3:
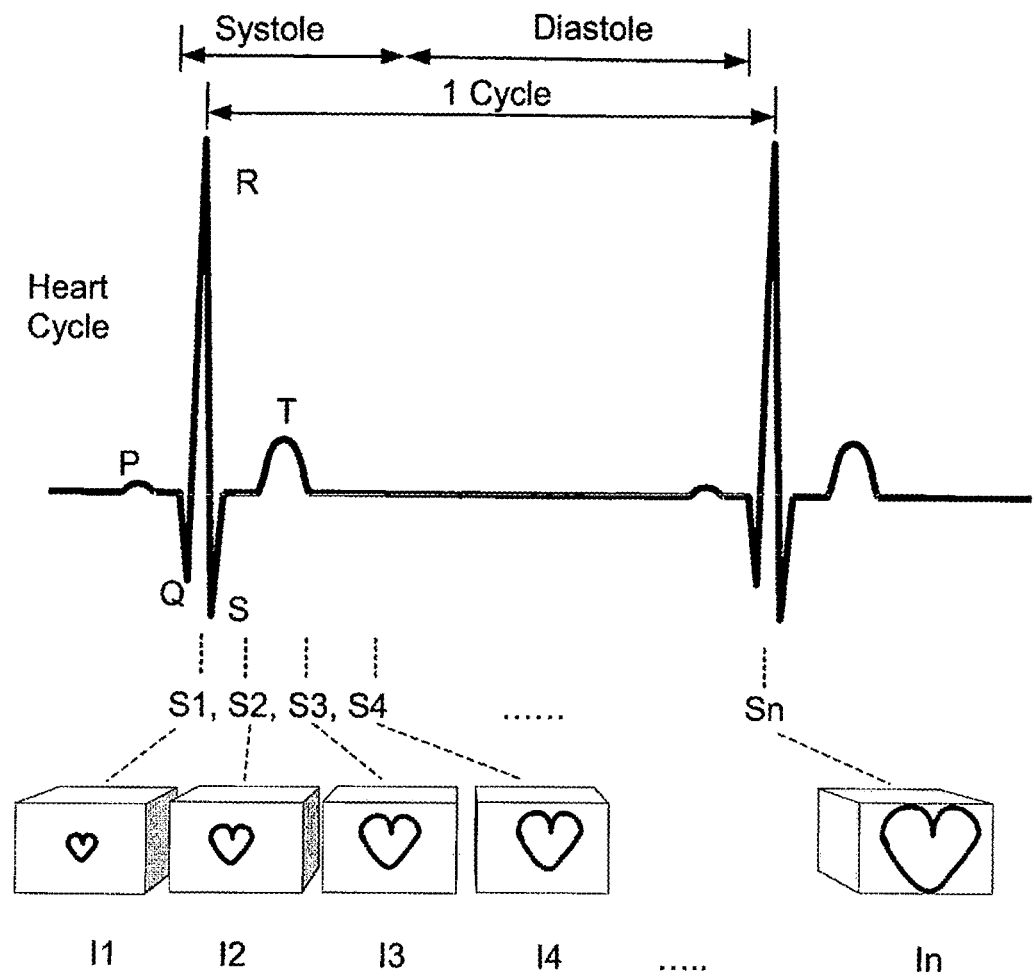
FIG. 3 is a schematic illustration of a sample of a periodic human characteristic signal associated (e.g., gated), with a set of images according to an embodiment.

Referring to FIGS. 2-3, in some embodiments, the imaging device 40 is configured to take a set of images (e.g., images I1, I2, I3 . . . In) of the target anatomy at distinct moments in time during the anatomy's periodic movement. For example, in some embodiments, each image of the set of images is taken in rapid succession. In another example, each image of the set of images can be taken at intervals over a specified time period. In this manner, the set of images can include images of the target anatomy during various stages of the anatomy's periodic movement, such as images associated with a complete cycle of the anatomy's periodic movement.

The imaging device 40 is configured to transmit (or transfer) the set of images to the processor 30. Similarly stated, the processor 30 is configured to received the images from the imaging device 40. In some embodiments, such as when the images are acquired pre-operatively, the processor 30 stores the received images in a memory 44 of the processor 30 (see, e.g., FIG. 2). The processor 30 is also configured to receive data via the converter 26. For example, the processor 30 can be configured to receive data associated with a periodic human characteristic signal. The periodic human characteristic signal can be, for example, a phase or a waveform of an ECG signal received from the patient 10 by the monitor 32 via the leads 34 coupled to the patient 10 and that is transmitted to the processor 30. In some embodiments, the human characteristic signal can be a signal associated with a heart beat, as shown in FIG. 3.

The processor 30 is configured to associate at least one image taken by the imaging device 40 with a sample of the periodic human characteristic signal to generate a gated signal sample. In this manner, a set of gated signal samples forms a gated dataset 42. In some embodiments, as illustrated in FIG. 3, each image of the set of images (represented as images I1, I2, I3, I4 . . . In) is associated with (or correlated to) a respective periodic human characteristic signal sample (represented as signal samples S1, S2, S3, S4 . . . Sn, respectively). In other words, the image 11 corresponds to the image that was taken at a moment of the patient's 10 ECG cycle that is represented by the signal sample S1. Similarly, the image 12 corresponds to the image that was taken at a moment of the patient's 10 ECG cycle represented by the signal sample S2, the image 13 corresponds to the image that was taken at a moment of the patient's ECG cycle represented by the signal sample S3, and so forth. As described in more detail herein, the gated dataset 42 can be used during the medical procedure for navigation and/or localization of the medical instrument 16 when the medical instrument 16 is used on the patient's body. For the sake of clarity of illustration, the designations of P, Q, R, S, and T are included in FIG. 3 to identify depolarizations and re-polarizations of the heart.

The processor 30 is also configured to receive data associated with at least one reference marker 18, 22, 24 that is transmitted to the processor 30. The data from the reference markers 18, 22, 24 can be transmitted, for example, via at least one of the tracker 20 and the converter 26. The data can include, for example, positional information associated with at least one of the reference markers (e.g., reference marker 18, 22, and/or 24).

The processor 30 includes a processor-readable medium storing code representing instructions to cause the processor 30 to perform a process. The processor 30 can be, for example, a commercially available personal computer, or a less complex computing or processing device that is dedicated to performing one or more specific tasks. For example, the processor 30 can be a terminal dedicated to providing an interactive GUI 31. The GUI 31 can be configured to display a multi-dimensional representation of the target anatomy based on the set of images stored in the memory 44. The GUI can also be configured to display a representation (or icon) 33 of a medical instrument, such as instrument 16, superimposed on an image of the target anatomy.

The processor 30, according to one or more embodiments of the invention, can be a commercially available microprocessor. Alternatively, the processor 30 can be an application-specific integrated circuit (ASIC) or a combination of ASICs, which are designed to achieve one or more specific functions, or enable one or more specific devices or applications. In yet another embodiment, the processor 30 can be an analog or digital circuit, or a combination of multiple circuits. In some embodiments, the processor 30 includes code with instructions to generate at least a portion of the gated dataset 42, such as generating at least one dataset vector associated with at least one image of the set of images taken by the imaging device 40. In some embodiments, the software includes code with instructions to choose an image that represents a current orientation of the live target anatomy utilizing information in the dataset 42, as described in more detail herein.

The processor 30 can include a memory 44 (schematically illustrated in FIG. 2). The memory 44 can include one or more types of memory. For example, the memory 44 can include a read only memory (ROM) component and a random access memory (RAM) component. The memory 44 can also include other types of memory that are suitable for storing data in a form retrievable by the processor 30. For example, electronically programmable read only memory (EPROM), erasable electronically programmable read only memory (EEPROM), flash memory, as well as other suitable forms of memory can be included within the memory component. The processor 30 can also include a variety of other components, such as for example, co-processors, graphic processors, etc., depending upon the desired functionality of the code.

The processor 30 can store data in the memory 44 or retrieve data previously stored in the memory 44. The components of the processor 30 can communicate with devices external to the processor 30 by way of an input/output (I/O) component (not shown). According to one or more embodiments of the invention, the I/O component can include a variety of suitable communication interfaces. For example, the I/O component can include, for example, wired connections, such as standard serial ports, parallel ports, universal serial bus (USB) ports, S-video ports, local area network (LAN) ports, small computer system interface (SCSI) ports, and so forth. Additionally, the I/O component can include, for example, wireless connections, such as infrared ports, optical ports, Bluetooth® wireless ports, wireless LAN ports, or the like.

The medical instrument 16 can be any suitable device used by the physician 14 during the IGI. At least a portion of the medical instrument 16 is configured to be disposed within the body of the patient. The medical instrument 16 can be any suitable medical device, including, but not limited to, a catheter, a needle, a stylet, a probe, a suction tube, an implant, an insert, a capsule, a sealant delivery device, a guidewire, a stent, a filter, an occluder, a retrieval device, a camera, a scope, a biopsy tool, a light source, and/or a lead. The medical instrument 16 can also be an instrument according to an embodiment, as described in detail herein. In some embodiments, for example, the medical instrument 16 is configured as a tubular member having a co-axial access path through which a biopsy needle can be inserted into the patient's body through the tubular member. For example, the tubular member can be configured as a co-axial therapy delivery system such that therapeutic agents can be delivered through the tubular member. In another example, the medical instrument 16 can be a catheter configured to be inserted into the right atrium of the patient's heart by way of the inferior vena cava and/or a femoral artery access point.

The tracker 20 is configured to detect (or track) the positional information of at least one of the reference markers 18, 22, 24. The tracker 20 can be any suitable tracking system, including, but not limited to, an electromagnetic tracking system. An example of a suitable electromagnetic tracking system is the AURORA® electromagnetic tracking system, commercially available from Northern Digital Inc. in Waterloo, Ontario, Canada. In some embodiments, the tracker 20 includes an electromagnetic field generator configured to emit a series of electromagnetic fields, which are designed to reach a portion of the body of the patient 10 at which at least one of the reference markers 18, 22, 24 is disposed. The electromagnetic field can, for example, induce a voltage in the at least one of the reference marker 18, 22, 24 that can be monitored and translated into a coordinate position of the at least one of the reference marker 18, 22, 24. In some embodiments, the tracker 20 includes a localizer (not shown), such as an optical, an acoustic, or another localizer depending upon the system for which the localizer is chosen. In some embodiments, the tracker 20 includes a transmitter coil array and/or a coil array controller.

The reference marker 18, also referred to herein as an instrument reference marker, is configured to be detected by the tracker 20. The reference marker 18 is disposed on and/or coupled to the medical instrument 16 in a known position. In this manner, a position, orientation, and/or location of the reference marker 18 (also referred to herein at the position or the positional information) as detected by the tracker 20 can be associated with a position of the medical instrument 16 with respect to the body of the patient 10. The positional information associated with the location, orientation, and/or position of the reference marker 18, and thus the medical instrument 16, can be identified by the tracker 20 and transmitted to at least one of the converter 26 and the processor 30. The reference marker 18 can be any suitable marker configured to be detected by the tracker 20. In some embodiments, for example, the reference marker 18 is or includes a coil, or an electromagnetic coil specifically, configured to receive an induced voltage, which voltage can be detected by the tracker 20.

The reference marker 22, also referred to herein as an external reference marker, is configured to be disposed at a location that is proximate to the target anatomy and that exhibits no or negligible movement with respect to the patient's heartbeat and/or respiration. In other words, the reference marker 22 is configured to be disposed at a static location. For example, in some procedures, the reference marker 22 can be securely fixed to a table 12 upon which the patient 10 is secured. In some procedures, for example if the patient 10 is not secured to the table 12, the reference marker 22 can be disposed on a portion of the patient's 10 static anatomy (e.g., a region of the patient's back). A position, location, and or orientation of the reference marker 22 is configured to be tracked by the tracker 20, as described herein. The reference marker 22 can be any suitable reference marker, such as any of the types of reference markers described herein.

The reference marker 24 is configured to be disposed in the region of the patient's body where the IGI will be performed. Specifically, the reference marker 24 is configured to be disposed at an anatomic location within the body of the patient 10 that exhibits movement correlated to and/or associated with a movement of the target anatomy (i.e., the anatomy intended for IGI). In some embodiments, the reference marker 24 is configured to be disposed at a location internal to the body of the patient. A position, location, and/or orientation of the reference marker 24 is configured to be detected by the tracker 20, as described herein. In some embodiments, the reference marker 24 can be any suitable reference marker, such as any of the types described herein. In some embodiments, for example, the reference marker 24 is a non-tissue internal reference marker, also referred to as a "fiducial," that is positioned within the body of the patient 10 and that is not made from the patient's bodily tissue.

Referring again to FIG. 1, at least one of the medical instrument 16, the reference markers 18, 22, 24, and/or the tracker 20 is couplable to the converter 26 of the system 100. The converter 26 is configured to receive a measurement, e.g., an analog measurement, from at least one of the reference markers 18, 22, 24 and/or the tracker 20. The converter 26 is configured to convert the analog measurement into digital data that can be received and/or processed by the processor 30, which is couplable to the converter 26. The converter 26 is also configured to transmit the digital data to the processor 30. The converter 26 can be, for example, a break-out box. In some embodiments, the converter 26 includes an isolator circuit, such as an isolator circuit of the type that may be included in a transmission line or a line carrying a signal or a voltage to another portion of system 100 (e.g., the processor 30). In some embodiments, the converter 26 is configured to electronically isolate at least the portion of the medical instrument 16 that is in contact with the patient 10 should an undesirable electrical surge or voltage occur. Although the converter 26 is illustrated as a distinct portion of system 100, in some embodiments, the converter is included in the processor 30, the medical instrument 16, and/or another suitable portion of system 100.

The monitor 32 is configured to be coupled to the body of the patient 10 and to the processor 30. The monitor 32 is configured to receive and/or monitor a periodic human characteristic signal from the patient 10. The periodic human characteristic signal can be, for example, a signal associated with at least one of heart beat and/or respiration. An example of a human characteristic signal is shown in FIG. 3. As illustrated in FIG. 1, the monitor 32 can be an ECG monitor configured to receive an ECG signal in the form of an ECG data transmitted to it by an ECG lead 34 coupled to the patient 10. In some embodiments, the monitor 32 is configured to transmit the periodic human characteristic signal (e.g., the ECG data) to the processor 30.

In preparation for conducting the IGI procedure, the reference marker 24 is placed in the gross anatomical region of interest for the procedure. After placement of the reference marker 24, a series of images of at least a portion of the body of the patient 10 is taken, produced, captured, and/or generated with the imaging device 40. The gated dataset 42 generated by the imaging device 40 is transferred to the processor 30. Optionally, at this point in the procedure, the patient 10 can be secured to operating table 12 and/or to portions of the system 100, including, for example, the tracker 20, the converter 26, the processor 30, the monitor 32, and/or the imaging device 40. The software of the processor 30 can begin an operation sequence. In some embodiments, the software first enters a Calibration State, as described below.

Figure 4:
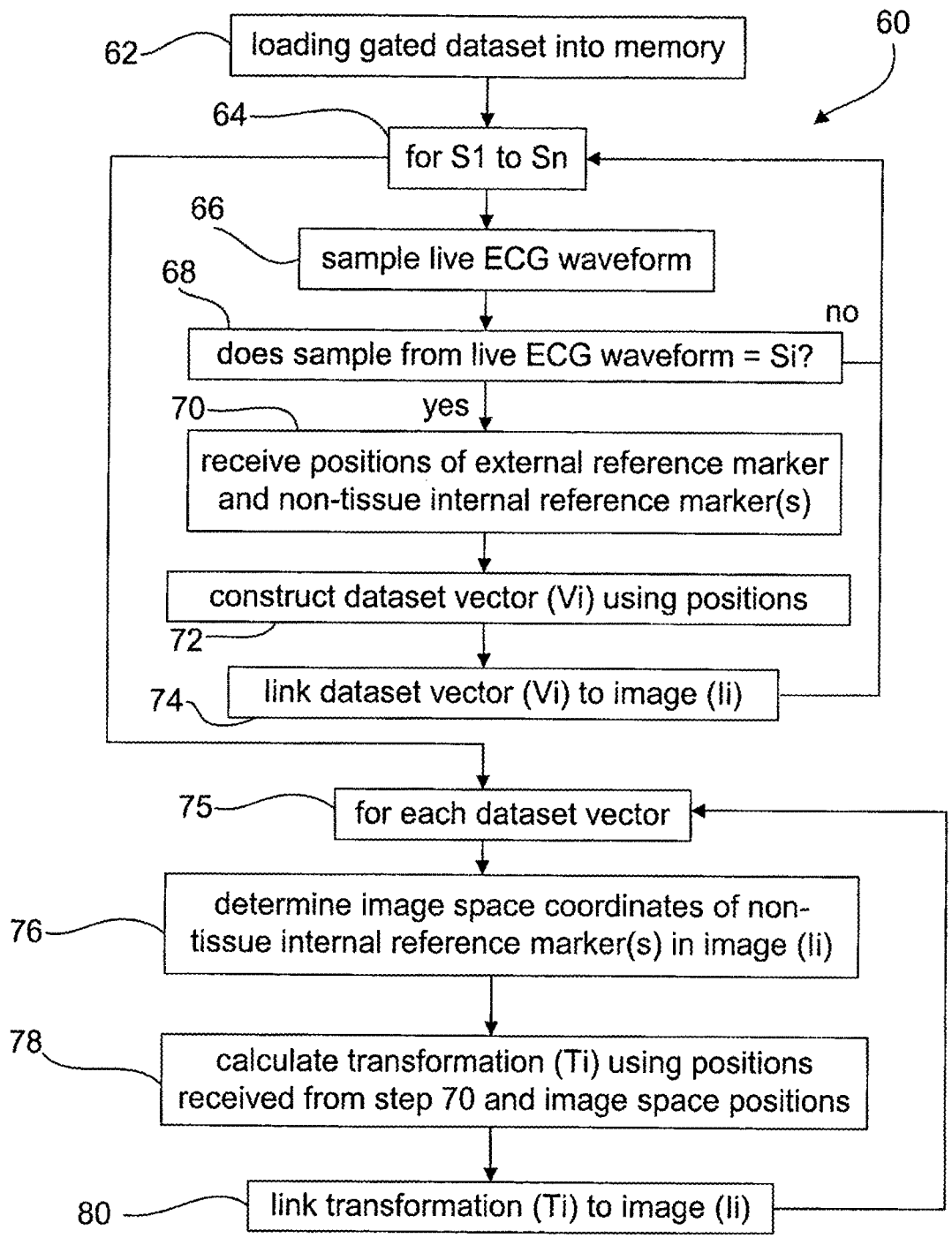
FIG. 4 is a flow chart of a method according to an embodiment.

FIG. 4 is a flow chart of a method 60 of performing the Calibration State. Although the activities of method 60 can be performed with any suitable system, for the sake of illustration, the activities of method 60 are described herein with reference to system 100 and FIGS. 1-3.

Referring to FIG. 4, the method 60 includes loading a gated dataset into a memory, 62. For example, referring to the system 100, in some embodiments, the code and/or software includes instructions to load the gated dataset 42 into the memory 44 of the processor 30. The method 60 optionally includes generating the gated dataset. The gated dataset can be generated by the imaging device, monitor, and/or processor, as shown and described above.

The method 60 also optionally includes looping through each gated signal sample, 64, and sampling a live periodic human characteristic signal, 66. For example, in some embodiments, the method includes looping through each gated signal sample S1, S2, S3 . . . Sn while a live periodic human characteristic signal is sampled and/or received from patient 10 via the monitor 32. The signal can be, similar to the periodic human characteristic signal used in generating the gated dataset 42 such as an ECG signal or waveform. In other words, a live ECG waveform can be sampled with respect to each gated signal sample used to construct the gated dataset.

The method 60 includes comparing the live periodic human characteristic signal sample to the gated dataset, 68. For example, referring to FIGS. 1-3, in some embodiments, the method includes comparing the live periodic human characteristic signal (e.g., the ECG waveform) sample of the patient 10 to a gated signal sample Si (e.g., sample S1, S2, or Sn) of the gated dataset 42. If the live periodic human characteristic signal matches the gated signal sample Si, the method continues, for example, to activity 70. If the live periodic human characteristic signal sample does not match the gated signal sample of the gated dataset 42, activities 64, 66 and 68 are repeated, for example, until a matching gated signal sample is detected. As used herein, the live periodic human characteristic signal is said to match the gated sample when the periodic human characteristic signal previously acquired is substantially equal to the live periodic human characteristic signal. A match can be ascertained using a signal processing technique that, in the case of an ECG waveform, examines historical waveform amplitudes. A match can occur, for example, when certain coordinates or other data associated with the samples to determine if the live sample and the gated sample are sufficiently equivalent for purposes of the IGI.

When the comparison of the live sample and the gated sample meets a specified criteria, the method 60 includes receiving a position of an external reference marker and a position of an internal reference marker, 70. For example, referring to the system 100, in some embodiments, the tracker 20 is polled for the position information after the live periodic human characteristic signal sample is matched to the gated signal sample. In some embodiments, the software queries the tracker 20 for the reference marker (e.g., reference marker 22, 24) positional information and the information is received by the processor 30.

Figure 4A:
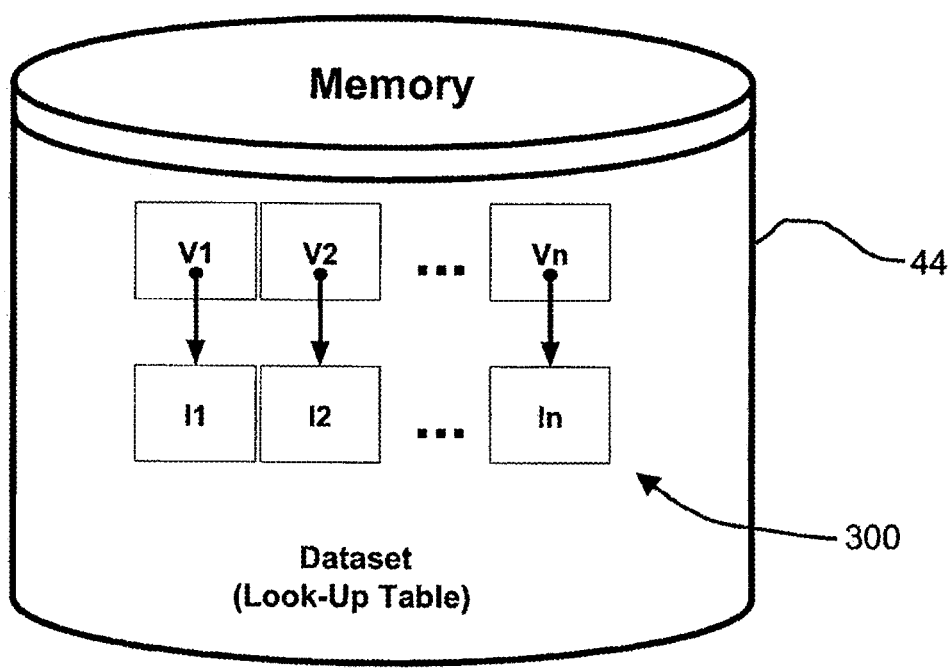
FIG. 4A is a schematic illustration of a dataset according to an embodiment stored in a portion of the system of FIG. 2.

The method 60 includes generating, calculating, and/or constructing a dataset vector associated with the positional information of the external reference marker and positional information of the internal reference marker, 72. Such positional information is also referred to herein as the tracking space coordinates. Referring to the system 100, in some embodiments, the code and/or software of the processor 30 can calculate a dataset vector Vi using the positional information of the external reference marker 22 and the internal reference marker 24. FIG. 4A shows a schematic illustration of a dataset including the dataset vector Vi. For example, each dataset vector can be characterized by a magnitude and a direction generated using data associated with the positional information of the external reference marker 22 and data associated with the positional information of the internal reference marker 24. Thus, the positional information of the external reference marker 22 can be characterized as an origin and the positional information of the internal reference marker 24 can be characterized as an end-point for a dataset vector that begins at the origin and ends at the end-point. In some embodiments, multiple internal reference markers are disposed within the body of the patient, thus multiple vectors may be generated.

The method 60 includes associating the dataset vector with an image that corresponds to (or that is associated with) the gated signal sample, 74. In some embodiments, a processor (e.g., processor 30) and/or a software program can store the dataset vector in a look-up table with a pointer to an image Ii (e.g., Image I1, I2 . . . In) that corresponds to the gated signal sample Si of gated dataset 42. For example, FIG. 4A shows a schematic illustration of a look-up table including the image Ii. In other words, the dataset vector is associated with a particular image Ii, thus the image can be referred to as a mapped image.

Optionally, the method 60 includes repeating the looping 64, the sampling 66, the matching 68, the receiving 70, the generating 72, and/or the associating 74 until each activity has been performed for each gated signal sample, and thus resulting in a set of dataset vectors stored in the look-up table. Each dataset vector of the set of dataset vectors is associated with an image that corresponds to the gated signal sample. Optionally, upon completion of activities 64 through 74 for each gated signal sample, the periodic human characteristic signal monitor 32 (e.g., ECG monitor) can be turned off or otherwise decoupled (or disconnected) from the system 100.

The method also includes performing a transformation calculation. In this manner, the method 60 also includes, for each dataset vector in the look-up table, examining each mapped image, 75. For example, each mapped image can be analyzed to identify data associated with the positional information of at least one of the external reference marker and the internal reference marker used to create the dataset vector with which the mapped image is associated.

The image space coordinate of the internal reference marker in each image is determined, 76. The image space coordinates can include, for example, voxel, volumetric pixel, and/or another suitable coordinate. For example, referring to system 100, the processor 30 can perform a segmentation procedure to identify the actual position data associated with the reference markers 22, 24 within the image dataset. Segmentation is the process of identifying reference points in the 3D image dataset. The purpose of the segmentation is to automatically locate potential "landmarks" in the dataset that indicate a location where a reference marker 22, 24 may be located. Segmentation can be performed in a variety of different manners, as described in detail in the '799 application. In some embodiments, the image Ii undergoes a thresh-holding segmentation during which the processor 30 determines (or finds) the image space coordinate of the internal reference marker 24 in the image Ii. In another example, the processor 30 can perform an automated segmentation procedure. For example, an automatic segmentation process can include, intensity filtering, connectivity analysis, and size and shape filtering to identify candidate marker locations, or image space coordinates of the marker candidates.

After the segmentation process is performed, an automatic correlation process can be performed. Correlation as used here is the process of matching and/or associating reference points between the image space and the tracking space. Matching and/or associating the reference points can aid in accurately computing the registration between the data in the image space and the data in the tracking space without user interaction. The correlation process determines where each of the reference markers 22, 24 (or a localization element coupled to each reference marker 22, 24) is positioned in the images. The correlation process can be used in the computation of a transformation between image space and tracking space. The apparatuses and methods described herein enable the correlation process to be automated with minimal user intervention. Automatic correlation results in an association of the location of the markers (e.g., reference markers 22, 24) in image space and tracking space, as well as the corresponding labeling/identification of each marker in each space.

After the correlation process, the processor 30 can perform an automatic registration process. The process of registration tracks temporal movement of the dynamic body part via the movement of the reference markers 22, 24. When temporally valid, the automatic registration process can compute the transformation between the tracking space and the image space. Thus, as illustrated in FIG. 4, the method 60 also includes calculating a transformation between the tracking space and the image space using the positional information of the external reference marker and the internal reference marker, 78. For example, in some embodiments, once the image space coordinate of the internal reference marker 24 is known, the positional information (e.g., the tracking space positions) of the external reference marker 22 and the internal reference marker(s) 24 received at activity 70 is used to calculate a transformation Ti between the tracking space and the image space. The transformation Ti can be calculated, for example, using a least squares method.

The method 60 includes associating the transformation with the image in question, 80. For example, the transformation Ti can be associated (or linked) to the image Ii. As such, the look-up table includes a dataset that includes the pre-operative images, at least one of the images (and, in some embodiments, each image) depicting the internal reference marker 24, being linked to a dataset vector and a transformation, and being at least 2D.

Figure 5:
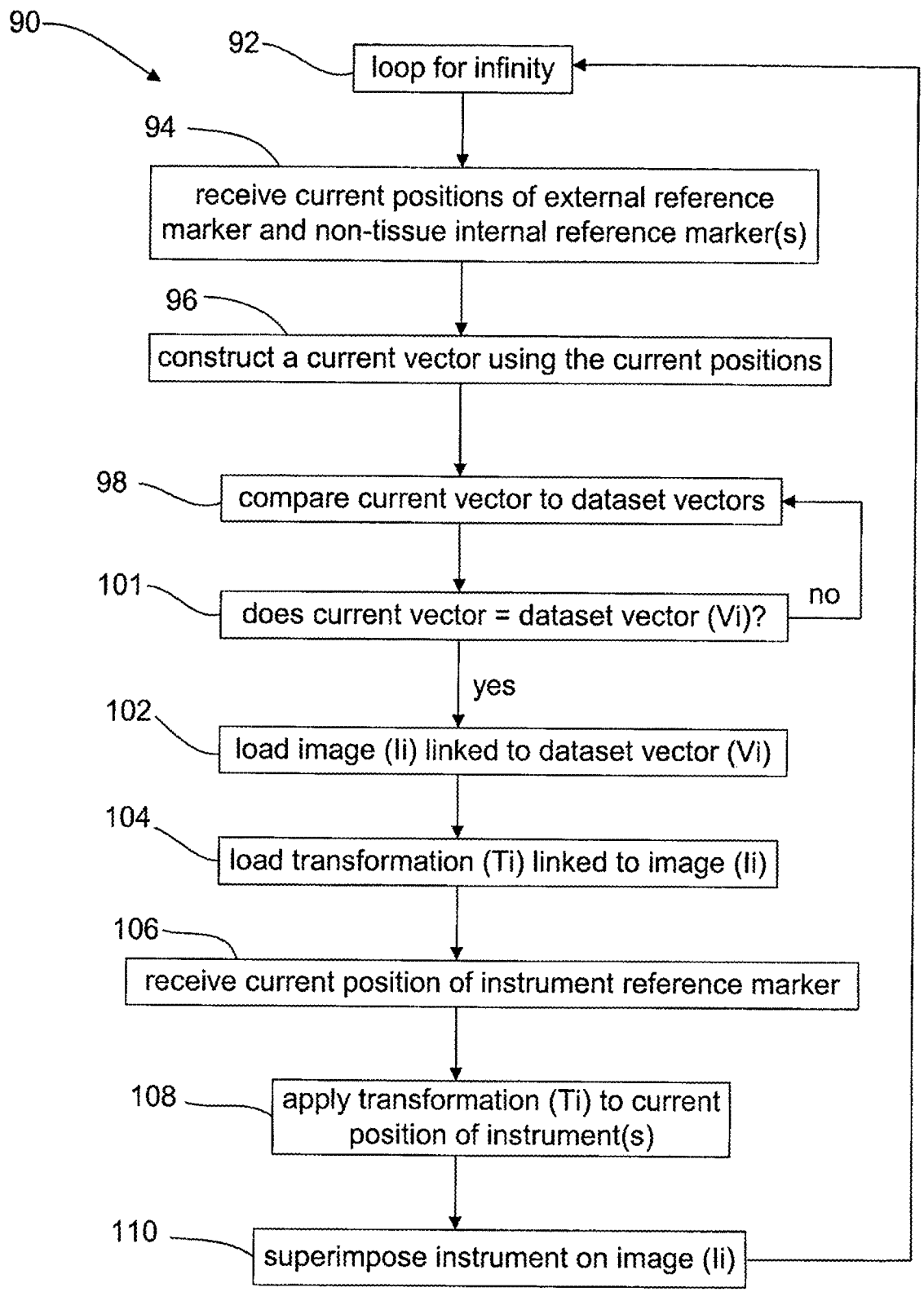
FIG. 5 is a flow chart of a method according to an embodiment.

FIG. 5 is a flow chart of a method 90 of performing the Navigation State. Although the activities of method 90 can be performed with any suitable system, for the sake of illustration, the activities of method 90 are described herein with reference to system 100 and FIGS. 1-3.

In the Navigation State, the method 90 can include an infinite loop of events, 92. The method includes receiving a current position of an external reference marker and a current position of an internal reference marker, 94. As used herein, "current" does not necessarily imply that the position of the external reference marker and the position of the internal reference marker are sampled and/or received at the same time (e.g., simultaneously and/or instantaneously), rather, the term "current" is used to differentiate between the positions received at this activity from the positions received at a previously completed activity, for example. For example, the processor 30 can obtain the position information as described above with respect to method 60, which can be different than the positional information received at activity 92.

Referring to FIG. 5, the method 90 includes constructing a current vector, 96. For example, in some embodiments, the method can include constructing a current vector using the current positions of the external reference marker and the internal reference marker received at activity 94. The method 90 includes comparing the current vector to the dataset vectors, 98. For example, in some embodiments, the software compares the current vector to the dataset vectors (e.g., V1, V2 . . . Vn) to determine the dataset vector associated with the current vector being analyzed. The generation of the dataset vectors is described above with reference to method 60 and FIG. 4A.

The method 90 also includes determining whether the current vector matches the dataset vector, 101. If the current vector does not match the dataset vector, the comparing of the current vector to the dataset vectors and the determining of the matching is repeated, e.g., until the current vector matches the dataset vector. If the current vector does match the dataset vector, the matching look-up table dataset vector (Vi) (or tracking space coordinates) is defined as the match dataset vector (MDV).

The method 90 includes loading an image from the gated dataset pointed to by (or associated with) the MDV, 102. Referring to the system 100, for example, in some embodiments, the method includes loading into the memory 44 of the processor 30 the image from the gated dataset 42 that is associated with (or pointed to by) the MDV.

Optionally, the method 90 includes loading the transformation associated with the MDV and the correlated image, 104. For example, in some embodiments, the method includes loading into the memory 44 of the processor 30 the transformation Ti associated with the MDV Vi and the correlated image Ii.

The method 90 includes receiving the current position of the instrument reference marker, 106. In some embodiments, referring to the system 100, for example, the processor 30 can receive the position of instrument reference marker 18 from the tracker 20 obtain (e.g., via the converter 26).

The method 90 also includes applying a transformation to the position of the instrument reference marker, 108. The transformation can be a transformation procedure as described above with reference to method 60. In some embodiments, the position of the instrument reference marker is transformed into image space. For example, in some embodiments, the software of the processor 30 applies the transformation Ti to the position of the instrument reference marker 18 to transform that position into image space.

The method 90 includes superimposing a representation of the instrument on the image, 110. For example, referring to FIG. 1, in some embodiments, the software of the processor 30 superimposes (e.g., renders, draws, or the like) a representation 33 (e.g., an iconic representation) of the medical instrument 16 on the selected image Ti displayed on the GUI 31 of processor 30.

Optionally, the activities of method 90, e.g., of the Navigation State, can be repeated. Repeated performance of the activities of method 90 can, for example, provide the physician 14 with a live representation of the medical instrument 16 with respect to the live position and orientation of the target anatomy, thus facilitating guidance of the medical instrument 16 to a desired location within the body of the patient, e.g., to deliver medical therapy and/or perform a medical procedure.

Figure 6:
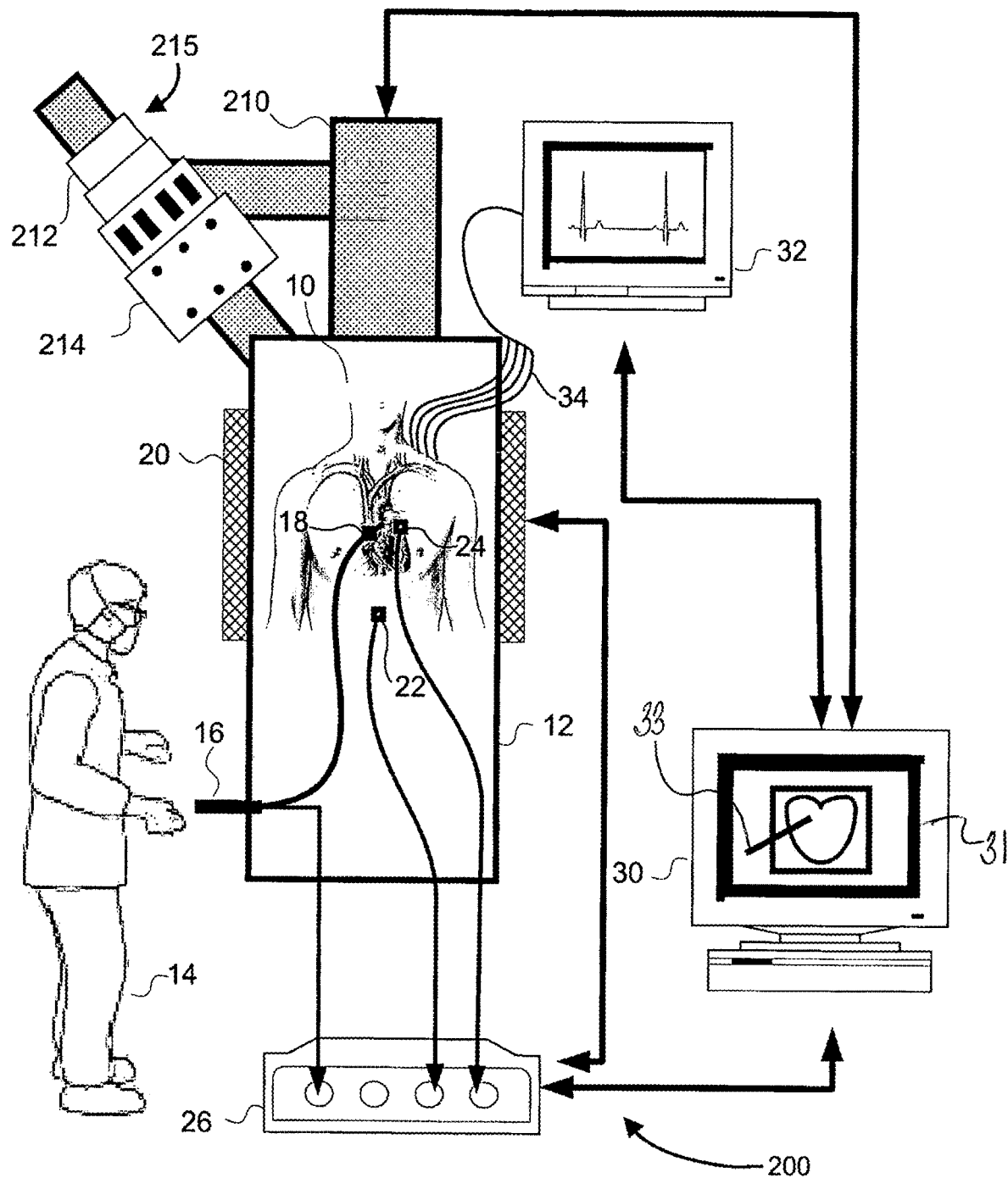
FIG. 6 is a schematic illustration of a system according to an embodiment, and a physician and a patient.

A system 200 according to an embodiment is illustrated in FIG. 6. The system 200 is configured to be used in performing and IGI using an imaging modality, such as CINE 2D fluoroscopy, that can be utilized within the operating theater during the medical procedure. In this manner, the physician 14 need not gate the periodic human characteristic signal to a pre-operative image, as described above with reference to system 100.

The system 200 is similar in many respects to system 100, except that the system 200 does not include association with the network 50. The imaging device is illustrated in FIG. 6 as a fluoroscope 215. The medical instrument 16, the reference markers 18, 22, 24, the converter 26, the monitor 32, and the processor 30, are configured to be coupled and in communication as described above. In some embodiments, the processor 30 includes software instead of or in addition to the software described above. For example, in some embodiments, the processor 30 includes software that comprises code providing instructions to perform a Calibration State 250 and/or a Navigation State 350 utilizing a fluoroscopy imaging modality, as described in more detail herein.

The fluoroscope 215 is coupled to the processor 30. The fluoroscope 215 includes a stand 210, a receiver unit 212 (e.g., a fluoroscope radiation receiver unit), and a calibration jig 214. The calibration jig 214 is couplable to the receiver unit 212. The fluoroscope 215 is configured to take at least one image of the target anatomy of the patient 10. For example, referring to FIG. 7, the fluoroscope 215 can be configured to take a set of images I1, I2 . . . In of the target anatomy.

Figure 7:
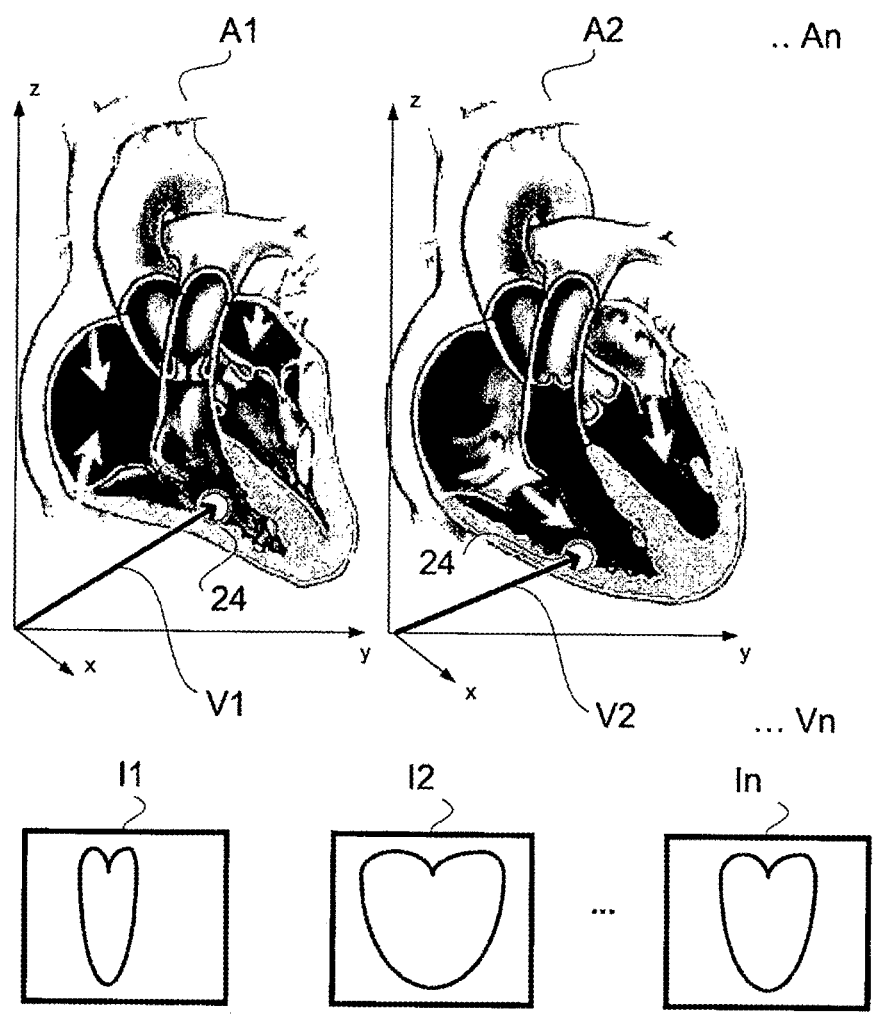
FIG. 7 is a set of images produced by the system of FIG. 6.

The internal reference marker, placed within the body as described above, is tracked by the tracker 20 as each image of the set of images I1, I2 . . . In is taken, produced, and/or generated with the fluoroscope 215. The placement of the internal reference marker 24 is illustrated in FIG. 7 with respect to the heart, and more specifically, with respect to various stages of the heart's function (A1, A2 . . . An). The vector (V1, V2 . . . Vn), described in more detail herein, can be determined based on the positions of each of the external reference marker (not shown) and the internal reference marker 24, as illustrated in FIG. 7 in terms of the X, Y, and Z axis information. Once the image is taken, an image most accurately depicting the target anatomy (e.g., the heart) at a particular moment in time can be ascertained by viewing the position of the internal reference marker 24 and selecting the image that was taken when the internal reference marker 24 was last in that particular location and orientation.

To begin the IGI, the patient 10 can be placed upon the table 12. Optionally, an ECG monitor 32 can be connected to the patient 10 for diagnostic purposes unrelated to performing image guidance. The fluoroscope 215 is positioned to allow images to be taken of patient 10. The physician 14 can select the appropriate orientation of the patient 10, such as a orienting the patient to obtain a Right Anterior Oblique (RAO) view. The physician 14 can place the external reference marker 22, as described above, at a location that exhibits no or minimal movement with respect to the patient's 10 heartbeat and/or respiration.

Figure 8:
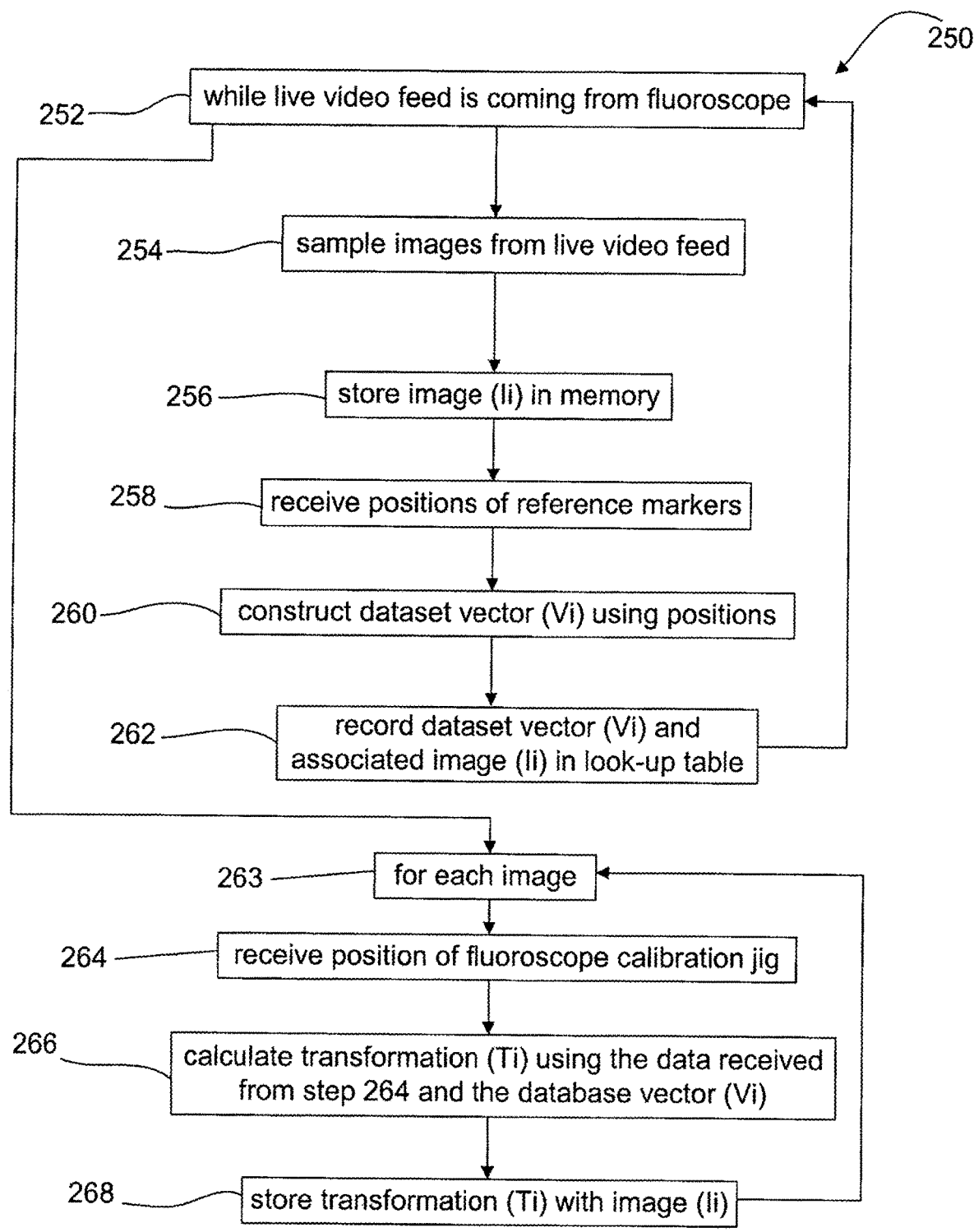
FIG. 8 is a flow chart of a method according to an embodiment.

FIG. 8 is a flow chart of a method 250 (e.g., a Calibration State) according to an embodiment. Although the activities of method 250 can be performed with any suitable system, for the sake of illustration, the activities of method 250 are described herein with reference to system 200. The method 250 includes receiving a live video feed from the fluoroscope, 252. For example, in some embodiments, the physician 14 can cause the fluoroscope 215 to begin acquiring an image signal (e.g., a CINE fluoroscopy loop). As the fluoroscope 215 begins to acquire the image signal, the live video feed can be sent to, and received by, the processor 30.

The method 250 includes sampling an image from the live video feed, 254. For example, in some embodiments, while the fluoroscope 215 is acquiring the CINE loop the method can include sampling the live video feed. In some embodiments, the sampling can occur at a rate greater than 30 Hz so as capture a number of images (e.g., image frames) that, when pieced together, appear to be a real time image to the human eye. As computing power makes faster sampling rates for more feasible, a sampling rate greater than 60 Hz can be implemented in accordance with Nyquist's Law.

The method 250 includes storing an image in memory, 256. The memory can be similar in many respects to memory 44, described above. In some embodiments, the method includes producing an image Ii, such as an image frame illustrated in FIG. 7, and storing that image into the memory 44 of the processor 30.

The method 250 includes receiving a position of a reference marker, 258. The receiving the position of the reference marker can be performed in a similar manner as described above with respect to method 60. In some embodiments, for example, the method can include receiving positional information associated with at least one of the reference markers 22, 24 from the tracker 20.

The method 250 includes constructing a dataset vector using the positional information of the reference markers, 260. For example, in some embodiments, the method includes constructing and/or calculating, a dataset vector Vi (e.g., dataset vector V1, V2 . . . Vn) that defines the orientation of the reference markers 22, 24 during the time of acquisition of the image Ii.

Figure 9:
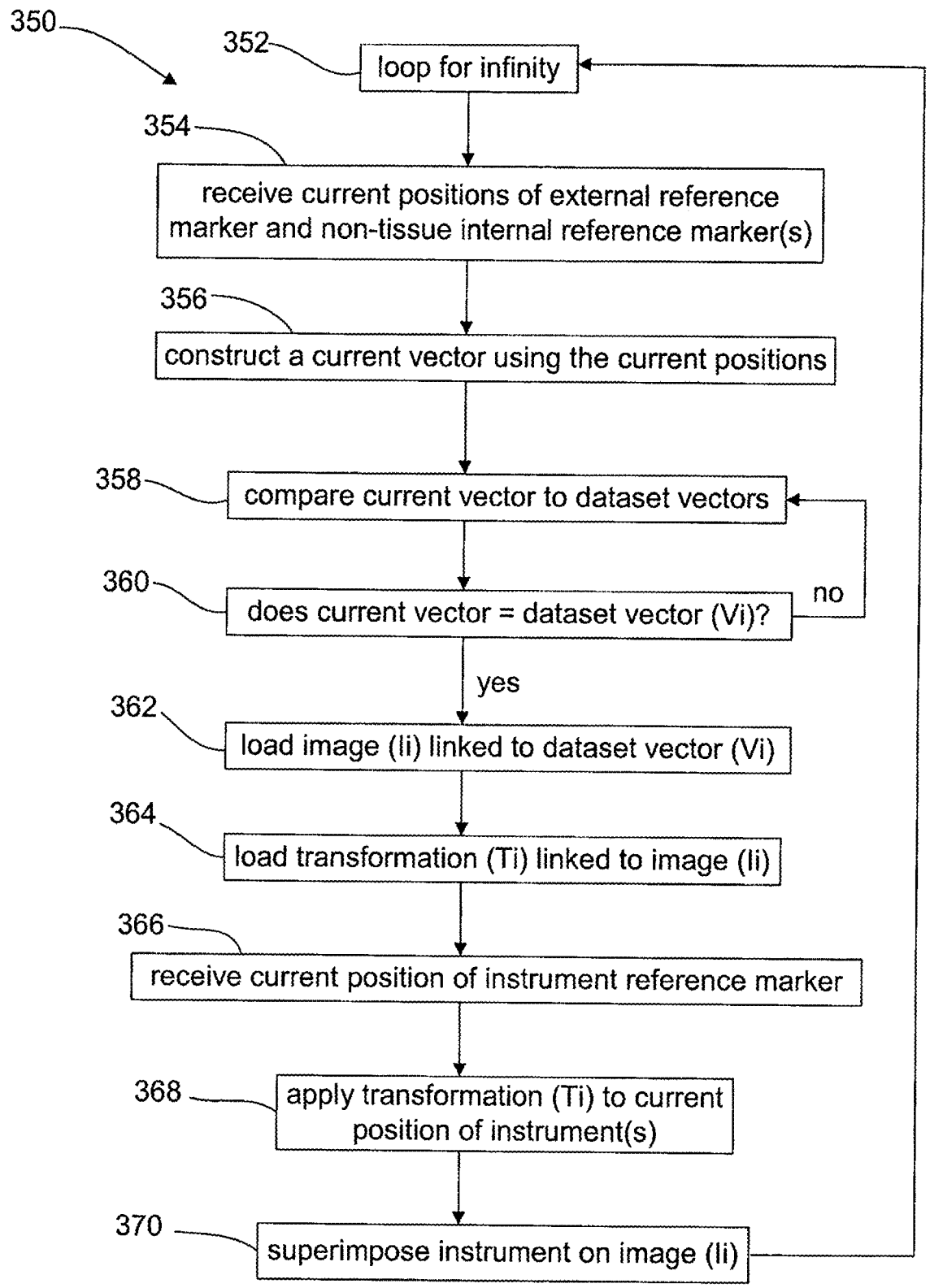
FIG. 9 is a flow chart of a method according to an embodiment.

The method 250 also includes recording the dataset vector and the associated image in a dataset, 262. For example, as shown in FIG. 4A, in some embodiments, the method includes recording the dataset vector Vi and the associated image Ii in a dataset 300. The dataset 300 can include, for example, a look-up table, as illustrated in FIG. 9 and described below. The dataset 300 can reside in the memory 44 of the processor 30. In some embodiments, the dataset 300 includes at least one image that depicts a non-tissue internal reference marker, is linked to positional information about the non-tissue internal reference marker, and is at least 2D.

Referring to FIG. 8, the software can initiate a transformation calculation process, e.g., for each image in a set of images, 263, after the set of images have been collected and/or stored. For example, the transformation can be implemented as described above with respect to method 60. In another example, the method 250 includes receiving a position of the calibration jig, 264. For example, referring to system 200, the code and/or software of processor 30 includes code comprising instructions to receive positional information associated with the position of the calibration jig 214 for each image Ii. In some embodiments, the software polls the tracker 20 for and receives from the tracker 20 the positional information of the calibration jig 214.

The method 250 includes calculating a transformation using the calibration jig positional information and the database vector, 266. In some embodiments, the software calculates a transformation Ti from a tracking space (e.g., the tracker field coordinate space) to image space (e.g., the fluoroscope image space) using the methods disclosed herein.

The method 250 also includes storing the transformation with the image, 268. For example, in some embodiments, the transformation Ti is stored in association with (e.g., linked to) the image Ti in the look-up table associated with the database vector Vi. In this manner, the transformation Ti is associated with the image Ii. The activities of method 250 can be repeated, for example, until the periodic cycle of movement of the target anatomy is captured by the images taken.

FIG. 9 is a flow chart of a method 350 according to an embodiment. The method 350 includes performing a Navigation State, which can be initiated by the code and/or software of the processor 30. Although the activities of method 350 can be performed with any suitable system, for the sake of illustration, the activities of method 350 are described herein with reference to system 200. In the Navigation State 350, the software can enter an infinite loop of activities, 352.

The method 350 includes receiving a current position of at least two reference markers, 354. The position information can be received, for example, in a manner similar to the receiving 94 described above with respect to method 90. In some embodiments, the processor 30 can receive positional information associated with the at least two reference markers from the tracker 20 via the converter 26. The processor can receive current position information, for example, that is associated with the position of each of the external reference marker 22 and the internal reference marker 24.

Referring to FIG. 9, the method 350 includes generating (or constructing) a current vector using the current positions, 356. The generating 356 can be implemented in a similar manner as the constructing 96 described above with respect to method 90. For example, the processor can construct a current vector using the received current positions of the external reference marker 22 and the internal reference marker 24.

The method 350 includes comparing the current vector to the dataset vectors, 358. The comparing 358 can be implemented in a similar manner as the comparing 98 described above with respect to method 90. For example, in some embodiments, the method includes comparing the current vector to the dataset vectors (e.g., V1 . . . Vn) to determine the dataset vector associated with the current vector being analyzed. In some embodiments, the method includes comparing the current positions of each of the external reference marker 22 and the internal reference marker 24 to the tracking space coordinates.

The method 350 includes determining as to whether the current vector matches the dataset vector, 360. The determining 360 can be implemented in a similar manner as the determining 101 described above with respect to method 90. If the current vector does not match the dataset vector, the comparing of the current vector to the dataset vectors and the determining of the matching is repeated, e.g., until the current vector matches the dataset vector. If the current vector does match the dataset vector, the matching look-up table dataset vector (Vi) (or tracking space coordinates) is defined as the match dataset vector (MDV).

The method 350 also includes loading an image from the dataset that is associated with the dataset vector, 362. The loading 362 can be implemented in a similar manner as the loading 102 described above with respect to method 90. For example, referring to system 200, in some embodiments, the method includes loading into the memory 44 of the processor 30 the image Ii from dataset 300 associated with (or pointed to by) the MDV (Vi).

Referring to FIG. 9, the method 350 optionally includes loading a transformation linked to the image, 364. The loading 364 can be implemented in a similar manner as the loading 104 described above with respect to method 90. For example, in some embodiments, the method includes loading into the memory 44 of the processor 30 the transformation Ti associated with the MDV Vi and the correlated image Ii.

The method 350 includes receiving the current position of the instrument reference marker, 366. The receiving 366 can be implemented in a similar manner as the receiving 106 described above with respect to method 90. In some embodiments, for example, the method includes receiving the position of instrument reference marker 18 from the tracker 20.

The method 350 includes applying a transformation to the position of an instrument reference marker, 368. The transformation can be a transformation procedure as described above with reference to method 60. In some embodiments, the position of the instrument reference marker 18 is transformed into image space. For example, in some embodiments, the code and/or software of the processor 30 applies the transformation Ti to the position of the instrument reference marker 18 to transform the position of the instrument reference marker 18 into image space.

The method 350 includes superimposing a representation of the instrument on the image, 370. The superimposing 370 can be implemented in a similar manner as the superimposing 110 described above with respect to method 90. For example, referring to FIG. 6, in some embodiments, the code and/or software of the processor 30 superimposes (e.g., renders, draws, produced, or the like) a representation (e.g., an iconic representation) of the medical instrument 16 on the selected image Ii displayed on the GUI 31 of processor 30.

Optionally, the activities of method 350, e.g., of the Navigation State, can be repeated. Repeated performance of the activities of method 350 can provide the physician 14 with a representation of the medical instrument 16 with respect to the live position and orientation of the target anatomy, thus facilitating guidance of the medical instrument 16 to a desired location within the body of the patient, e.g., to deliver medical therapy and/or perform a medical procedure.

Although the methods illustrated and described herein include automatic registration of the images, in other embodiments, the images can be registered with a different registration process. For example, in other embodiments, the images can be registered using point registration, surface registration, pathway registration, auto-registration, or the like, or any combination thereof.

Although the systems (e.g., systems 100, 200) and the methods (e.g., methods 60, 90, 250, 350) have been illustrated and described as including and with respect to a single internal reference marker 24, in other embodiments, a system and/or a method can include any suitable number of reference markers, e.g., two, three, or more reference markers.

Figure 10:
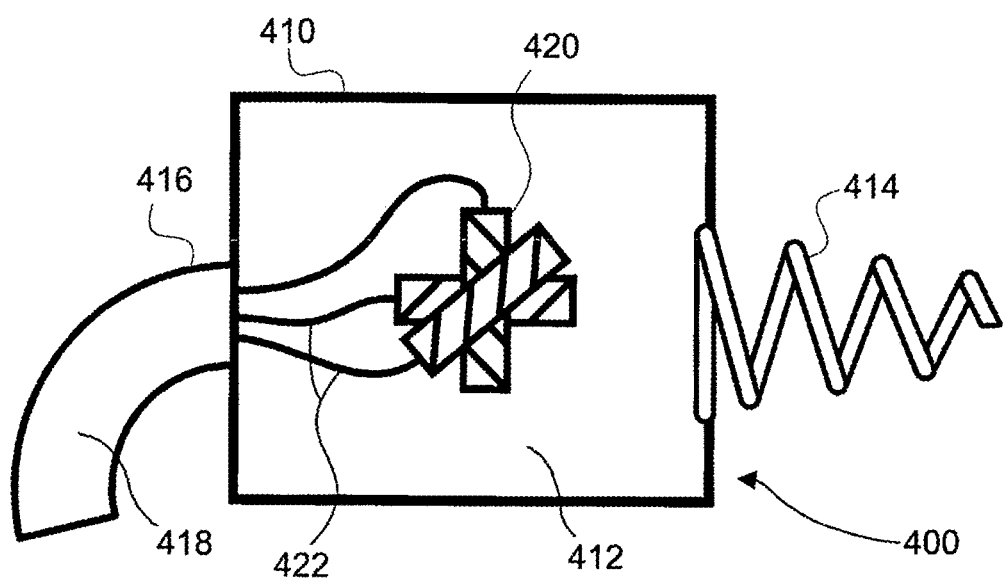
FIG. 10 is a front view of a portion of the system of FIG. 1.

The reference marker 24 can be similar in many respects to the reference marker 400 shown and described below with reference to FIG. 10. The reference marker 400 includes a body portion 410, a fixation member 414, and a channel portion 416. The body portion 410 defines a chamber 412. The chamber 412 is configured to receive at least a portion of a medical device, such as a sensor 420. The body portion 410 of the reference marker 400 is configured to be opaque to the imaging device 40. In other words, the body portion 410 is configured to be visible (e.g., as a blank or white spot) on an image of a portion of the body of the patient including the reference marker 400 taken produced, and/or generated using and imaging device (e.g., imaging device 40). For example, the body portion 410 can be constructed of a material that is opaque to the imaging device 40. In some embodiments, the body portion 410 is constructed of platinum, titanium, or the like, or the like, or any suitable combination thereof.

The fixation member 414 is coupled to the body portion 410. The fixation member 414 is configured to facilitate retention of the reference marker 400 within the body of the patient (not shown). Similarly stated, the fixation member 414 is configured to limit movement of the body portion 410 relative to the body of the patient. As illustrated in FIG. 10, the fixation member 414 has a pig-tail shape. In this manner, the fixation member 414 is configured to be screwed into a portion of the patient's body (e.g., in bone and/or cartilage) and/or unscrewed to release the reference marker 400 from the patient's body, such as after completion of the procedure. Although the fixation member 414 of the reference marker 400 is illustrated and described herein as having a pig-tail shape, in other embodiments, the fixation member can have any suitable configuration for retaining the reference marker within the body of the patient.

The channel portion 416 of the reference marker 400 is coupled to the body portion 410. The channel portion 416 defines a passageway 418 that is in fluid communication with the chamber 412 of the body portion 410. The channel portion 416 is configured to receive at least a portion of a medical device, such as sensor 420. The channel portion 416 can include, for example, a sheath or a portion of a sheath. The channel portion 416 can be constructed of any suitable material, including, for example, plastic.

The channel portion 416 can be of any suitable configuration (e.g., length, circumference, etc.). In some embodiments, for example, the channel portion 416 can have a length such that the channel portion 416 is configured to extend from a location within the body of the patient to a location exterior to the body of the patient. In this manner, the sensor 420 (or other medical device) can be inserted into the passageway 418 of the channel portion 416 outside of the body of the patient and delivered to the chamber 412 of the body portion 410 of the reference marker 400 after implantation of the reference marker 400 within the body of the patient. In some embodiments, the sensor 420 can be inserted into the chamber 412 after images of the target anatomy have been taken to generate the gated dataset 42. For the sake of clarity, as used herein, references to the reference marker 400 should be construed as references to those portions of the reference marker that are disposed within the body of the patient during a given IGI.

The sensor 420 can include at least one connecting lead 422 configured to facilitate disposing the sensor 420 in the chamber 412. The sensor 420 and/or the connecting leads 422 can be secured in place with respect to the chamber 412. In some embodiments, at least one of the sensor 420 and the lead 422 can be constructed of a ferrous material. In other embodiments, however, because the sensor 420 and/or lead 422 can be inserted into the chamber 412 of the body portion 410 of the reference marker 400 after generation of the gated dataset 42 (and thus after imaging by the imaging device 40), the sensor 420 and/or lead 422 need not be constructed of a non-ferrous material.

In use, the chamber 412 is implanted within the body of the patient, e.g., prior to imaging with the imaging device 40. At the time of implantation, the chamber 412 of the reference marker 400 can be empty. After implantation, the reference marker 400 can be imaged (or scanned) with the imaging device 40, such as when the imaging device 40 is taking pre-operative images of the target anatomy. Upon completion of the imaging, the sensor 420 (or other medical device) is inserted through the passageway 418 until at least a portion of the sensor 420 is disposed within the chamber 412 of the body portion 410 of the reference marker 400.

Each of the body portion 410 and the fixation member 414 can be constructed of any suitable material configured to be disposed within a body of a patient and/or configured to be used with an imaging device (e.g., a gated scanner 40). In some embodiments, for example, at least one of the body portion 410 and the fixation member 414 is constructed of a non-ferrous material. In this manner, the reference marker 400 is configured to comply with safety requirements of certain imaging modalities, such as an MRI device. In other words, the body portion 410 of the reference marker 400 can be constructed of a material suitable for imaging with the imaging device 40, while the sensor 420 can be constructed of a material suitable for being detected by the tracker 20 (and which may or may not be suitable for imaging with the imaging device).

Although portions of the systems (e.g., systems 100, 200) are illustrated and described herein as being distinct from other portions of the system (e.g., system 100, 200), in some embodiments, a portion of the system may be incorporated into another portion of the system. For example, in some embodiments, portions of the system (e.g., the tracker 20 and/or the processor 30 of systems 100, 200) can be incorporated into the imaging device 40. In this manner, an integrated imaging and tracking system can be provided.

Although the imaging device 40 has been illustrated and described as being and ECG-gated imaging device, in other embodiments, the system can include an imaging device having a different gated configuration. In other words, the system can be gated with a different periodic human characteristic signal. For example, in some embodiments, the gate triggering event (or the period human characteristic signal) can be a physiologically-related signal associated with the patient's 10 respiration or hemodynamics. For example, a sensor regarding respiration may be used to trigger the acquisition of the images at the same point in the respiration cycle. A sensor can be coupled to the system 100, such as an external capnographic sensor that monitors exhaled $CO_2$ concentration and/or an airway pressure sensor, that is configured to determine the end expiration point. The respiration, both ventriculated and spontaneous, can cause an undesirable elevation or reduction, respectively, in a baseline pressure signal, which can be used to trigger acquisition of the image(s). By measuring systolic and diastolic pressures at the end expiration point, the coupling of respiration noise is minimized.

Furthermore, any suitable imaging modality configured to be gated to a periodic human characteristic signal may be used in performance of the methods described herein, including, but not limited to CT, MRI, CINE fluoroscopy, positron emission tomography (PET), ultrasound, and functional MRI (fMRI).

In another example, although method 60 has been illustrated and described as generating the dataset vector associated with the position and/or location of the external reference marker and/or the position and/or location of the internal reference marker, 72, in some embodiments, the generated dataset vectors include only the positional coordinates of the external reference marker and the internal reference marker, thus the generating the dataset vector need not be performed and the associating of the dataset vectors to the various images of gated dataset includes associating the positional (or tracking space) coordinates of the relevant reference markers to those images. Similarly, although method 90 has been illustrated and described as comparing the current vector to the dataset vectors, 98, in some embodiments, the current positions of the external reference marker and the internal reference marker are compared to the tracking space coordinates.

The systems (e.g., system 100, system 200) and methods (e.g., methods 60, 90, 250, 350) described herein can be used in performing a variety of medical procedures using IGI. For example, in some embodiments, a system (e.g., system 100, system 200) and/or a method (e.g., methods 60, 90, 250, 350) described herein is used to deliver a sealant to a body of a patient. In some embodiments, for example, the medical instrument 16 is used in conjunction with a navigation system (e.g., system 100, 200) according to an embodiment to deliver the sealant to the body of the patient.

A medical instrument 500 configured to deliver a sealant to a body of a patient according to an embodiment is illustrated in FIG. 11. For example, the instrument 500 can be configured to deliver at least one surgical sealant, including, but not limited to a fibrin sealant, thrombin, fibrinogen, a cyanocrylate, collagen (or a collagen-based compound), a cross-linker, an aldehyde, and/or a hydrogel, or the like, or any combination thereof. A suitable sealant for a particular procedure can be selected, for example, based on certain properties of the sealant. Such properties can include, for example, the strength of the sealant; whether the sealant is biodegradable; the degree, if any, to which the sealant facilitates natural healing of a bodily wound; the sealant's barrier against infection; and/or the ease of use of the sealant.

For example, in some embodiments, the instrument 500 can deliver a fibrin sealant, which can include thrombin and fibrinogen, may have suitable properties for the procedure to be performed, such as, for example, properties related to tissue adhesion and/or hemostasis. The materials included in the fibrin sealant can be of any suitable origin, e.g., human plasma, bovine, or another suitable source. The fibrin sealant also can be configured to promote healing of a bodily wound. In some embodiments, and as described in more detail herein, fibrin sealant can be delivered to a puncture site formed within the lung to seal the lung. In some embodiments, the fibrin sealant can be delivered to the body of the patient as a liquid. In other embodiments, in other embodiments, the fibrin sealant can be delivered to the body of the patient as a slurry, suspension, paste or the like.

In another example, the instrument 500 can deliver a sealant including a cyanoacrylate, which can be configured to form a seal within the body of the patient for a period of about seven to ten days. The cyanocrylate sealant can be substantially water-proof and/or water-resistant, have a high strength (e.g., a strength greater than the fibrin sealant), and/or be non-bioresorbable. In some embodiments, the cyanocrylate sealant is configured to stop bleeding at the portion of the patient's body on which the sealant is disposed. For example, the sealant can include a coagulant. In some embodiments, the cyanocrylate sealant can be delivered to the body of the patient via a substrate.

In yet other embodiments, the instrument 500 can deliver a sealant including a collagen and/or a collagen-based compound. In some embodiments, the collagen-based sealant is configured to deliver fibrinogen to the body of the patient. The sealant can include any suitable known collagen-based compound, including, but not limited to FloSeal, commercially available from Sulzer Spine Tech, Proceed, commercially available from Fusion Medical Technologies, and Costasis, commercially available from Cohesion Technologies.

In yet other embodiments, the instrument 500 can deliver a sealant including an aldehyde, such as gluteraldehyde. In some embodiments, the aldehyde sealant is configured to fill an opening within the patient's body, such as a puncture site. In some embodiments, the aldehyde sealant is configured to be delivered to the body of the patient as a liquid. In some embodiments, the aldehyde sealant is configured to be disposed on an outer surface of a medical instrument, such as in a coating on an outer surface of a biopsy needle. The sealant can include any suitable known aldehyde, including, but not limited to a glutaraldehyde glue, such as, for example, the glutaraldehyde glue marketed under the name BioGlue®.

In still other embodiments, the instrument 500 can deliver a sealant including any suitable hydrogel. In some embodiments, the hydrogel is constructed of and/or includes a polyethylene glycol polymer, which has sealant properties that are configured to be activated upon exposure to a light source. In some embodiments, the sealant including the hydrogel can be configured to be bioabsorbable. In some embodiments, the sealant including the hydrogel is configured to be delivered to the body of the patient as a liquid. In some embodiments, the sealant can be or include the hydrogel marketed under the name Focal Seal-L, commercially available from Gynzyme Bioscience.

The instrument 500 includes a first shaft 502, a second shaft 512, a reference marker 524, and a sensor 526. The first shaft 502 defines a lumen 504 and an opening 506 in communication with the lumen 504 of the first shaft 502. At least a portion of the first shaft 502 is disposable within the body of the patient.

The second shaft 512 defines a lumen 516, a chamber 514, and an opening 518 in communication with the chamber 514 of the second shaft 512. The chamber 514 of the second shaft 512 is configured to receive the sealant (not shown). In use, the sealant can be disposed within the chamber 514 prior to disposing the first shaft 502 within the body of the patient. For example, in some embodiments, the sealant can be conveyed into the chamber 514 via the opening 518 before the first shaft 502 and/or the second shaft 512 are disposed within the body. In other embodiments, the sealant is disposed in the chamber 514 while the first shaft 502 and/or the second shaft 512 are disposed within the body of the patient, e.g., via an injection source.

The lumen 516 of the second shaft 512 is fluidically isolated from the chamber 514 of the second shaft 512. The lumen 516 of the second shaft 512 is configured to receive a medical instrument. For example, the lumen 516 of the second shaft 512 can receive at least one of a light source, a scope, a biopsy tool, a camera, or the like. In this manner, the second shaft 512 provides access for the medical instrument to the body of the patient. For example, in some embodiments, a light source can be received in and/or passed through the lumen 516 of the second shaft such that the light source is proximate to the sealant delivered to the body of the patient.

The second shaft 512 is configured to be received within the lumen 504 of the first shaft 502. In some embodiments, the second shaft 512 is tightly engaged with the first shaft 502. In other words, the second shaft 512 is not freely movable with respect to the first shaft 502 in the absence of a force (e.g., a force applied by the physician to move the second shaft 512). The second shaft 512 has a first position, as shown in FIG. 13, in which the opening 518 of the second shaft 512 is fluidically isolated from the opening 506 of the first shaft 502. The second shaft 512 has a second position (not shown in FIGS. 11-13) in which the opening 518 of the second shaft 512 is in fluid communication with the opening 506 of the first shaft 502. When the second shaft 512 is in the second position, the opening 506 of the first shaft 502 and the opening 518 of the second shaft 512 define a flow passageway for the sealant. The flow passageway is configured to permit movement of the sealant from the chamber 514 of the second shaft 512 to a location exterior to the first shaft 502.

In some embodiments, the second shaft 512 is movable with respect to the first shaft 502 in at least one rotational direction, as indicated by arrow $A_1$ in FIG. 13. For example, the second shaft 512 can be configured to rotate in at least one of a clockwise or a counter-clockwise direction. The second shaft 512 is moved from its first position to its second position by rotating the second shaft 512 with respect to the first shaft 502. In use, the second shaft 512 is moved to its second position to deliver the sealant to the body of the patient. In other embodiments, the second shaft 512 is movable with respect to the first shaft 502 in at least one longitudinal direction.

The reference marker 524 is disposed on at least one of the first shaft 502 or the second shaft 512. In the embodiment illustrated in FIG. 11, the reference marker 524 is disposed on an outer surface of the first shaft 502. The reference marker 524 is configured to be viewed by an imaging device (not shown) that is exterior to the body of the patient when the reference marker 524 is disposed within the body of the patient. For example, the reference marker 524 can be configured to be viewed by any imaging device (or modality) described herein, such as imaging device 40. In some embodiments, the reference marker 524 is similar in many respects to the instrument reference marker 18, described herein.

The sensor 526 is coupled to a distal end portion 503 of the first shaft 502. The sensor 526 is configured to sense a pressure within a portion of the body of the patient at which the sensor 526 is disposed. The sensor 526 can be any suitable known pressure sensor, such as, for example a piezo-electric pressure transducer. In some embodiments, the sensor 526 is configured to sense a first pressure at a first portion of the body of the patient and a second pressure at a second portion of the body of the patient. Thus, the sensor 526 can be characterized as being configured to detect a spatial change in pressure within the body of the patient. In some embodiments, the sensor 526 is configured to sense a first pressure at a first time at an area within the body of the patient at which the sensor is disposed and a second pressure at a second time different than the first time at the area within the body of the patient. Thus, the sensor 526 can be characterized as being configured to detect a temporal change in pressure within the body of the patient. In this manner, the sensor 526 can facilitate delivery of the sealant because the sensor 526 can provide an indication of a desired status of a target anatomy (e.g., exhalation of the lungs) and/or an indication of a desired location of the instrument with respect to the target anatomy (e.g., when the sensor of the instrument detects the second pressure indicating the sensor of the instrument has moved from a position inside the lung to a position proximate to the surface of the lung).

Although the instrument 500 is illustrated and described as including a second shaft 512 defining a lumen 516, in other embodiments, a third shaft is disposed within at least one of the first shaft or the second shaft. In this manner, the second shaft need not include the lumen as described herein. The third shaft can be movable with respect to at least one of the first shaft and the second shaft.

Figure 14:
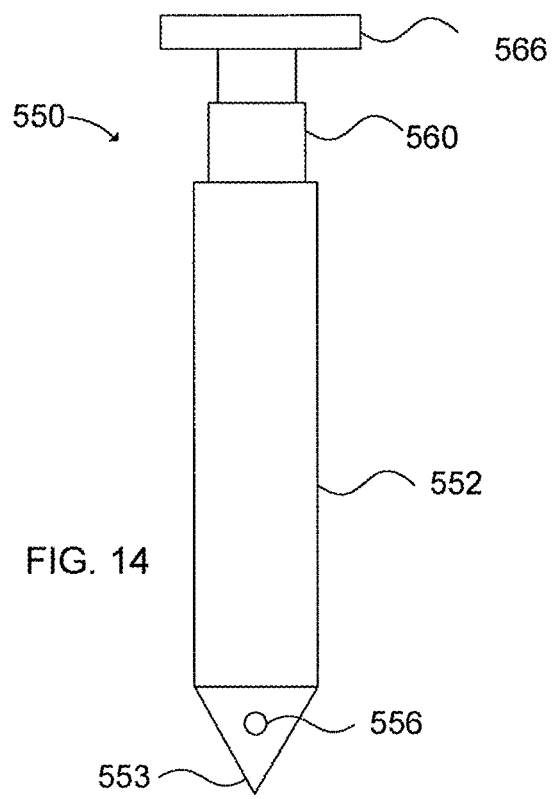
FIG. 14 is a front view of an apparatus according to an embodiment.
Figure 15:
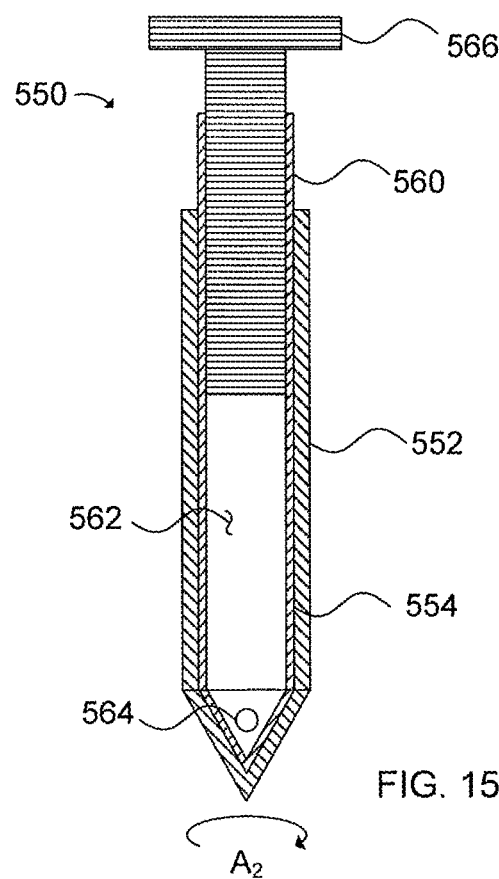
FIG. 15 is a cross-sectional view of the apparatus of FIG. 14.

A medical instrument 550 configured to deliver a sealant to a body of a patient according to an embodiment is illustrated in FIGS. 14-15. The instrument 550 includes a first shaft 552, a second shaft 560, and a plunger 566. The first shaft 552 defines a lumen 554 and an opening 556 in communication with the lumen 554 of the first shaft 552. The first shaft 552 defines a tapered distal tip 553. The tapered distal tip 553 is configured to pierce, puncture and/or displace bodily tissue. In this manner, the instrument 550 is configured to penetrate a bodily tissue (e.g., the skin, the lung). Although the tapered distal tip 553 is shown as being sharp, in other embodiments, the tapered distal tip 553 can include a slightly rounded tip.

The second shaft 560 defines a chamber 562 and an opening 564 in communication with the chamber 562. The chamber 562 is configured to receive a sealant. The sealant can be any suitable sealant described herein. At least a portion of the second shaft 560 is received within the lumen 554 of the first shaft 552. The second shaft 560 is movable with respect to the first shaft 552 in at least one rotational direction, as indicated by arrow $A_2$ in FIG. 15, and as described above with respect to instrument 500. The second shaft 560 is configured to be rotated with respect to the first shaft 552 to align the opening 564 of the second shaft 560 with the opening 556 of the first shaft 552. In this manner, the aligned openings 556, 564 form a flow passageway through which the sealant can move from the chamber 562 to an area external to the first shaft 552.

At least a portion of the plunger 566 is disposed within the chamber 562 of the second shaft 560. The plunger 566 is configured to be translationally moved with respect to the second shaft 560. The plunger 566 can be moved in a distal direction, for example, such that a portion of the plunger 566 contacts the sealant received in the chamber 562. In this manner, the plunger 566 is configured to facilitate delivery of the sealant to the body of the patient.

Figure 16:
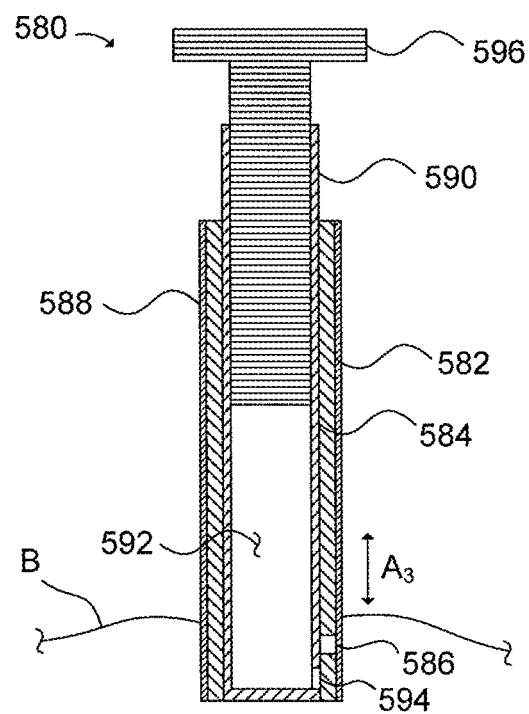
FIG. 16 is a cross-sectional view of an apparatus according to an embodiment.

Although the second shafts described above (e.g., second shaft 512, 560) have been illustrated and described as being movable with respect to the first shafts described above (e.g., first shaft 502, 552) in at least one rotational direction, in other embodiments, as illustrated in FIG. 16, a medical device 580 according to an embodiment includes a second shaft 590 that is movable with respect to the first shaft 582 in at least a one translational direction, as indicated by arrow A.sub.3. For example, in some embodiments, the second shaft 590 is configured to be translationally moved with respect to the first shaft in at least one of a proximal direction or a distal direction. The second shaft 590 is moved from a first position in which an opening 594 defined by the second shaft 590 is fluidically isolated from an opening 586 defined by the first shaft 582 to a second position in which the opening 594 of the second shaft 590 is in fluid communication with the opening 586 of the first shaft 582 by translating the second shaft 590 with respect to the first shaft 582. In some embodiments, the second shaft 590 can be moved from its first position to its second position by translationally moving a handle portion 596 coupled to the second shaft 590 (e.g., in at least one of the distal or the proximal directions).

The first shaft 582 is configured to define an opening within the bodily tissue of the patient. In some embodiments, as illustrated in FIG. 16, the first shaft 582 includes a coating 588 disposed on at least a portion of the outer surface of the first shaft 582. The coating 588 is configured to form a seal between the portion of the first shaft 582 and a portion of the body B of the patient in contact with the outer surface of the portion of the first shaft 582 when the first shaft 582 defines and/or is disposed within the opening of the bodily tissue.

In some embodiments, the seal is formed in response to the coating 588 being exposed to a bodily fluid. In some embodiments, the coating 588 includes the sealant. For example, the coating 588 can include at least one of thrombin, fibrinogen, a cyanocrylate, collage, a cross-linker, an aldehyde, or a hydrogel, or the like, or any combination of the foregoing.

At least one of the coating 588 or the sealant has a first physical state prior to the coating 588 being exposed to the bodily fluid (or contacting the body B) and a second physical state different than the first physical state after the coating is exposed to the bodily fluid. For example, in some embodiments, the coating 588 can include a solid material disposed on an outer surface of a portion of the first shaft 582 (e.g., a biopsy needle) and can include the sealant in the form of a liquid and/or gel within a matrix of the solid coating 588. The coating 588 can be configured to change from the first solid physical state to a second physical state, e.g., a liquid, in response to being exposed to the bodily fluid. As the coating 588 is liquefied, the sealant is released from the matrix, and thus delivered to the body part B (e.g., skin, a lung, a heart). In another example, the coating 588 and the sealant are solidified on the outer surface of the medical instrument 580 (e.g., a catheter). As the sealant is exposed to the bodily fluid (e.g., blood, mucous, or the like) the sealant is changed from its first physical state, e.g., solid, to its second physical state, e.g., liquid, and the seal is formed between the first shaft 582 and a portion of the body B of the patient in contact with the outer surface of the portion of the first shaft 582. Although the coating 588 is shown as being disposed about substantially all of the first shaft 582, in other embodiments, the coating 588 can be disposed about only a portion of the first shaft 582.

While various embodiments have been described herein, it should be understood that they have been presented by way of example only, and not limitation. Where methods described herein indicate certain events occurring in certain order, the ordering of certain events may be modified. Additionally, certain of the events may be performed concurrently in a parallel process when possible, as well as performed sequentially as described above. Furthermore, although methods are described above as including certain events, any events disclosed with respect to one method may be performed in a different method according to the invention. Thus, the breadth and scope should not be limited by any of the above-described embodiments. While the invention has been particularly shown and described with reference to specific embodiments thereof, it will be understood that various changes in form and details may be made.

For example, although the at least one of the coating 588 or the sealant is described herein as changing from the first physical state to the second physical state in response to exposure to the bodily fluid, in other embodiments, the coating and/or the sealant can be configured to change physical states in response to a different agent. For example, in some embodiments, at least one of the coating or the sealant is configured to change from the first physical state to the second physical state upon placing the coating and/or the sealant in contact with the body B, and/or upon placing the coating and/or sealant in contact with a second coating that is disposed on another medical instrument or on the body of the patient. In some embodiments, the change in physical state is caused by a chemical reaction between a material included in at least one of the coating 588 and the sealant and a bodily or other fluid (e.g., saline) or another material. In yet other embodiments, the change in physical state of the coating 588 can be caused by a thermal reaction (e.g., heating of the outer surface of the first shaft 582). For example, in some embodiments, the first shaft 582 can include a heater configured to allow a user to selectively increase the temperature of the outer surface of the first shaft 582 to trigger the change in the physical state of the coating 588.

Although the delivery instruments (e.g., instruments 500, 550, 580) have been illustrated and described herein as including at least two co-axial shafts, in other embodiments, a delivery instrument can include non-coaxial shafts and/or any suitable number of shafts. For example, in some embodiments, a delivery instrument includes a first shaft defining a lumen and a second shaft and third shaft, each disposable within the lumen of the first shaft. The second shaft can define a chamber that contains a sealant, and the third shaft can be configured to receive a medical instrument (e.g., a scope). In another example, a delivery instrument can include a first shaft having a longitudinal axis and a second shaft configured to be at least partially disposed within a lumen of the first shaft. The second shaft can have a longitudinal axis that is non-coaxial with and/or nonparallel to the longitudinal axis of the first shaft. For example, the longitudinal axis of the second shaft can be parallel to the longitudinal axis of the first shaft. In another example, the longitudinal axis of the second shaft can be transverse to the longitudinal axis of the first shaft. In another example, a delivery instrument includes a first shaft and a second shaft disposed adjacent the first shaft. Each of the first shaft and the second shaft defines a lumen. The lumen of the first shaft and the lumen of the second shaft are each configured to be in fluid communication with a lumen of a third shaft. For example, a first sealant material can be disposed in the lumen of the first shaft and a second sealant material can be disposed in the lumen of the second shaft. At the time of delivery of the sealant to the target anatomy, at least a portion of the first sealant material is moved to the lumen of the third shaft and at least a portion of the second sealant material is moved to the lumen of the third shaft. In this manner, the first sealant material and the second sealant material can be combined prior to delivery of the sealant to the target anatomy.

Although the second shaft 512 of instrument 500 is illustrated and described as defining the lumen 516, in other embodiments, the second shaft can define any suitable number of lumens, e.g., two, three, or more. In other embodiments, the second shaft 512 of the instrument 500 can be devoid of a lumen.

Although the lumen 516 of the second shaft 512 of instrument 500 is illustrated and described herein as being fluidically isolated from the chamber 514 of the second shaft 512, in some embodiments, the lumen of the second shaft is configured to be placed in fluid communication with the chamber of the second shaft.

Although the instrument 500 is illustrated and described herein as including the reference marker 524 on at least one of its first shaft 502 or its second shaft 512, in other embodiments, the instrument includes any suitable number of reference markers on its first shaft and/or its second shaft, e.g., two, three, or more reference markers. In other embodiments, the instrument 500 need not include any reference markers.

Figure 17:
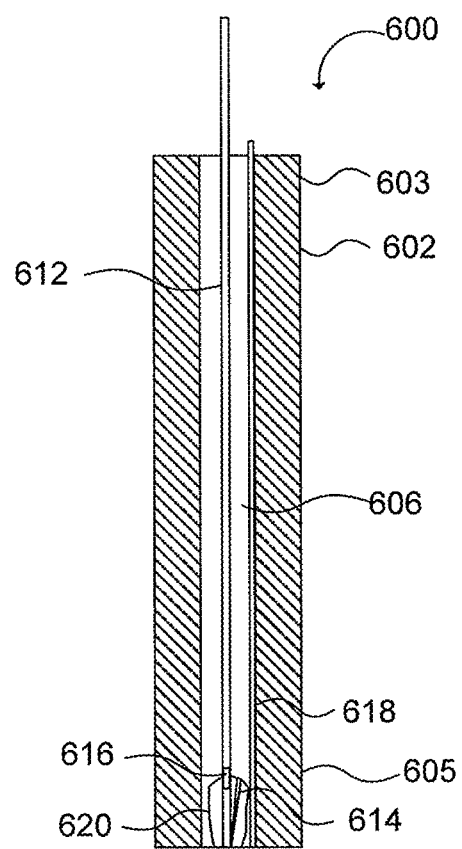
FIGS. 17 and 18 are cross-sectional views of an apparatus according to an embodiment in a first configuration and a second configuration, respectively.
Figure 18:
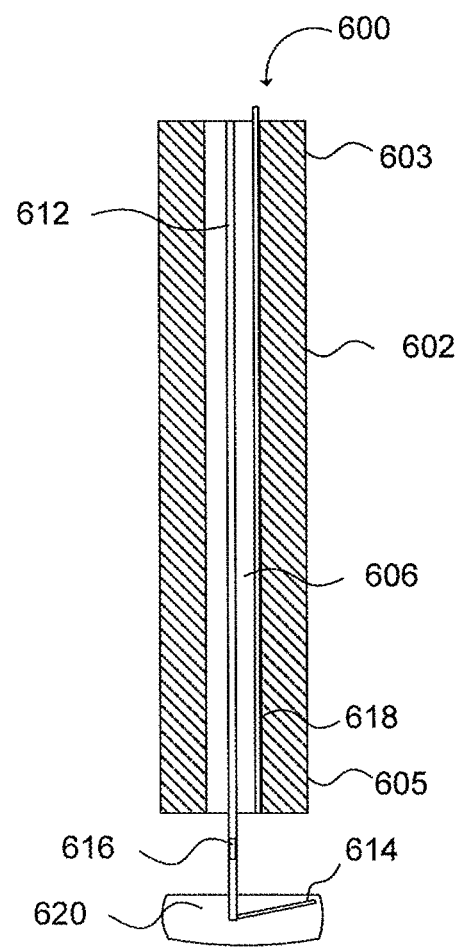

A medical instrument 600 configured to deliver a seal member 620 to a body of a patient according to an embodiment is illustrated in FIGS. 17-18. The instrument 600 includes an elongate shaft 602, a delivery mechanism 612, a reference marker 616, a sensor 618, and a seal member 620. The elongate shaft 602 has a proximal end portion 603 and a distal end portion 605 and defines a lumen 606. At least a portion of the elongate shaft is disposable within the body of the patient.

The delivery mechanism 612 is movable with respect to the elongate shaft 602 and includes a protrusion 614. Additionally, the protrusion 614 is movable with respect to the remainder of the delivery mechanism 612. In some embodiments, the delivery mechanism 612 is movably coupled to the elongate shaft 602. In some embodiments, the delivery mechanism 612 is a stylet, an expandable wire mechanism, or the like. The delivery mechanism 612 is movable between a first configuration (illustrated in FIG. 17) and a second configuration (illustrated in FIG. 18). The protrusion 614 is extended from the delivery mechanism 612 at a first angle when the delivery mechanism 612 is in its first configuration. For example, in some embodiments, the first angle can be an angle between zero and 89 degrees (i.e., an acute angle) with respect to the remainder of the delivery mechanism 612. In other embodiments, for example, the first angle can be an angle 90 degrees or greater with respect to the delivery mechanism. The protrusion 614 is extended from the delivery mechanism 612 at a second angle greater than the first angle when the delivery mechanism 612 is in its second configuration. In some embodiments, the protrusion 614 of the delivery mechanism 612 is biased towards being extended from the delivery mechanism 612 at the second angle. Similarly stated, in some embodiments, the protrusion 614 is biased in the second configuration.

The delivery mechanism 612 is configured to move the seal member 620 between a collapsed configuration (illustrated in FIG. 17) and an expanded configuration (illustrated in FIG. 18) when the delivery mechanism 612 is moved from its first configuration to its second configuration. In some embodiments, the movement of the protrusion 614 from its first position to its second position, and thus movement of the seal member 620 from its collapsed configuration to its expanded configuration, is similar to the operation of an umbrella.

The seal member is configured to seal an opening within the body of the patient when the seal member 620 is in its expanded configuration. At least a portion of the seal member 620 is disposed within the lumen 606 of the elongate shaft 602 when the seal member is in its collapsed configuration, as illustrated in FIG. 17. In other words, at least a portion of the seal member 620 is deformable for delivery of the seal member 620 to the bodily tissue.

Figure 19:
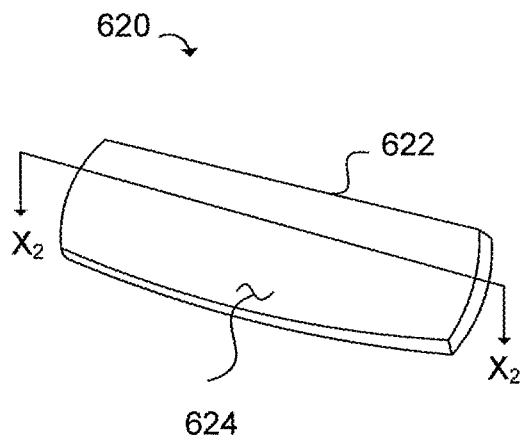
FIG. 19 is a perspective view of a portion of the apparatus of FIGS. 17 and 18.
Figure 20:
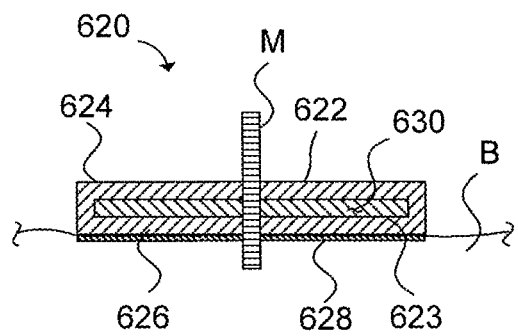
FIG. 20 is a cross-sectional view of the portion of the apparatus illustrated in FIG. 19 taken along line X.sub.2-X.sub.2, and a cross-section of a portion of a medical instrument.

As illustrated in FIGS. 19-20, the seal member 620 includes a substrate 622 and a sealant 630 disposed on a portion of the substrate 622. The substrate 622 couplable to a bodily tissue of the patient. In some embodiments, for example, the substrate 622 is couplable to a dynamic bodily tissue (e.g., the lung, the heart) within a bodily cavity of a patient. In another example, the substrate 622 is configured to be disposed on an interior surface of an organ of the patient. For example, the substrate 622 can be disposed on an interior surface of the lung of the patient.

The substrate 622 has a first surface 624 and a second surface 626 different than the first surface 624. An adhesive 628 is disposed on the second surface 626 of the substrate 622. The adhesive 628 is configured to couple the substrate adjacent to the bodily tissue (e.g., the dynamic bodily tissue). At least a portion of the substrate 622 is configured to be penetrated by a medical instrument M (see e.g., FIG. 20). Said another way, the substrate 622 is configured to maintain its structural integrity and/or retain its functional qualities (e.g., being coupled to the bodily tissue B) when the medical instrument M is inserted through the substrate 622.

As illustrated in FIG. 20, the sealant 630 is disposed in a cavity 623 defined by the substrate 622 between the first surface 624 of the substrate 622 and the second surface 626 of the substrate. In some embodiments, the sealant 630 is a liquid or a gel sealant disposed in the cavity 623 of the substrate 622. The sealant 630 can be any suitable known sealant of the types shown and described herein.

The sealant 630 is configured to be penetrated by the medical instrument M when the medical instrument M is inserted through the substrate 622. The sealant 630 is configured to substantially prevent passage of a material through an opening in the substrate 622 formed by the medical instrument M. In other words, the sealant 630 forms a seal about the portion of the medical instrument M inserted through the sealant 630, e.g., between the medical instrument M and the substrate 622. In this manner, the seal member 620 is configured to substantially prevent the passage of an environmental contaminant through the opening defined by the medical instrument and into the body of the patient. Also in this manner, the seal member 620 is configured to substantially prevent the passage of a bodily fluid from an area inside the body of the patient through the opening defined by the medical instrument.

Referring again to FIGS. 17-18, the delivery mechanism 612 includes the reference marker 616. The reference marker 616 is configured to be viewed by an imaging device (e.g., imaging device 40, described herein) that is exterior to the body of the patient when the reference marker 616 is disposed within the body of the patient. The reference marker 616 can be, for example, any suitable reference marker described herein.

The sensor 618 is coupled to the elongate shaft 602. At least a portion of the sensor 618 is disposed on the distal end portion 605 of the elongate shaft 602. The sensor 618 is configured to detect a pressure at a location within the body of the patient proximate to the distal end portion 605 of the elongate shaft 602 (and/or a portion of the delivery mechanism 612). The sensor 618 can be any suitable sensor, for example, a sensor according to an embodiment (e.g., sensor 524) described herein.

In some embodiments, the medical instrument M (or another medical instrument) can be received in the elongate shaft 602 of the instrument 600. For example, in some embodiments, the medical instrument M can be received in the lumen 606 of the elongate shaft 602 alongside the delivery mechanism 612. In another example, the medical instrument M can be received in the lumen 606 of the elongate shaft 602 prior to placement of the delivery mechanism 612 within the lumen 606 of the elongate shaft 602 and/or after removal of the delivery mechanism 612 within the lumen 606 of the elongate shaft 602. The medical instrument M can be any suitable medical instrument described herein, including, but not limited to, a light source, a scope, a biopsy tool, a camera, or the like. For example, the instrument 600 can be used in conjunction with a scope to facilitate placement and/or delivery of the sealant 630 to a target anatomy.

Although the sealant 630 is illustrated and described as being disposed within the cavity 623 of the substrate 622, in other embodiments, the sealant can be disposed on a different portion of the substrate. For example, in some embodiments, the sealant is disposed on at least one of the first surface or the second surface of the substrate.

Although the adhesive 628 is illustrated and described as being disposed on the second surface 626 of the substrate 622, in other embodiments, the adhesive can be disposed on a different portion of the substrate. For example, in some embodiments, the adhesive is disposed on the first surface of the substrate. In still other embodiments, the seal member includes no adhesive.

Although the instrument 600 is illustrated and described as including a single elongate shaft 602, in some embodiments, an instrument for delivering a seal member includes at least two elongate shafts. For example, in some embodiments, the instrument includes a first elongate shaft configured to pierce and/or penetrate the bodily tissue. In some embodiments, the first elongate shaft is configured to biopsy the bodily tissue. The second elongate shaft is disposable within a lumen of the first elongate shaft. The first elongate shaft can be at least partially withdrawn from being disposed about the second elongate shaft. The second elongate shaft can be configured to deliver the seal member, e.g., as described herein with respect to instrument 600. In use, the physician can at least partially withdraw the first elongate shaft, e.g., until a distal end portion of the first elongate shaft contacts a surface of the bodily tissue. The seal member is moved to its expanded configuration and delivered to the bodily tissue with the second elongate shaft.

Although the protrusion 614 of the delivery mechanism 612 is illustrated and described herein as being movable with respect to the delivery mechanism 612 between a first angle and a second angle, in other embodiments, a delivery mechanism can include a protrusion differently configured for moving the seal member from the collapsed configuration to the expanded configuration. For example, in some embodiments, the delivery mechanism includes a spring protrusion. The spring protrusion is compressed by a shaft of the instrument when the protrusion is disposed within the shaft of the instrument. The spring protrusion is configured to move to a non-compressed or expanded position when the spring protrusion is no longer compressed by the shaft of the instrument. In this manner, the spring protrusion is configured to move the seal member to its expanded configuration when the spring protrusion is moved to its non-compressed position.

Although the seal member 620 has been illustrated and described herein as being delivered to a tissue within the body of the patient and using the instrument 600, in other embodiments, the seal member can be delivered to a surface of the body of the patient (e.g., the skin) with any suitable instrument or without the assistance of an instrument. For example, in some embodiments, the seal member 620 can be disposed over an area of the patient's skin through which the medical instrument M will be inserted. The second surface 626 of the substrate 622 is placed against the skin and can be configured to seal against the skin. For example, the adhesive 678 can be configured to adhere to the skin. As the medical instrument M is inserted through the seal member and into the body of the patient, a seal is formed between the sealant 630 and the medical instrument. Thus, the seal member substantially prevents air or other potentially harmful elements from entering the patient's body at the entry site. In other embodiments, the physician can make an incision through the seal member 620 and the skin. In still other embodiments, the seal member 620 can be pre-cut with an incision slot (not shown) so that the physician can make an incision in the skin through the pre-cut slot.

Figure 21:
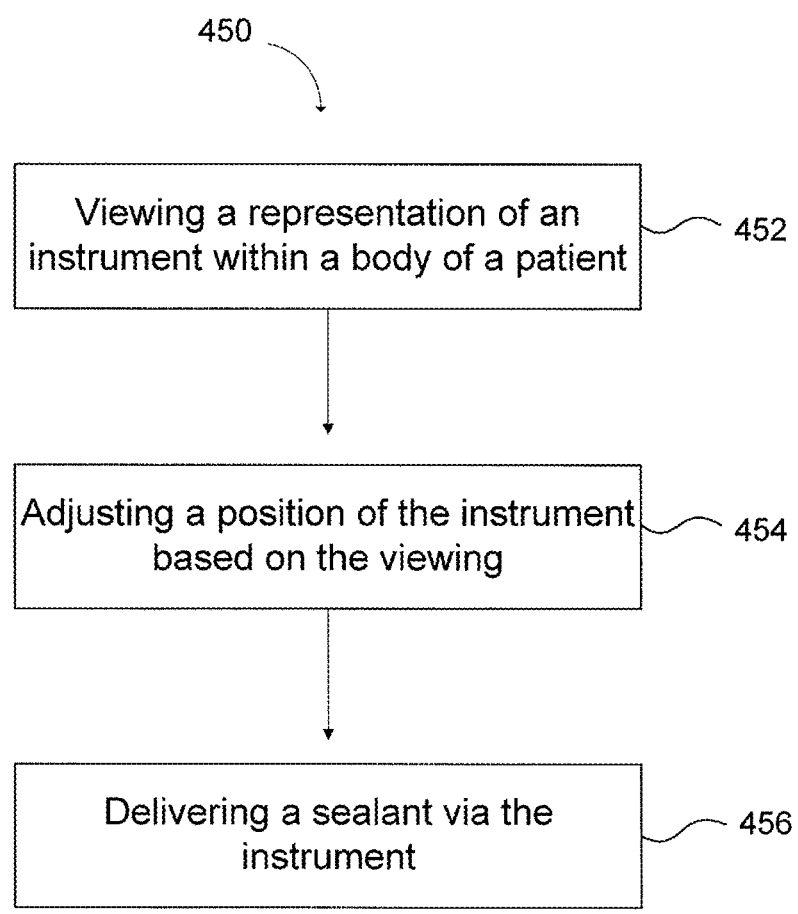
FIG. 21 is a flow chart of a method according to an embodiment.

Methods according to embodiments include delivering a sealant to a bodily opening utilizing a medical instrument in conjunction with a system and/or a method for IGI described herein. For example, FIG. 21 is a flow chart of a method 450 according to an embodiment. The method 450 includes viewing a representation of an instrument within a body of a patient, 452. The instrument can be any suitable medical instrument described herein (e.g., instruments 16, 500, 550, 600). The representation is superimposed on an image of a set of images associated with a cyclical movement of a body part (e.g., the targeted anatomy), for example as described above with respect to method 250 and/or method 350. The image is associated with a MDV. The MDV, as described in detail above, is the dataset vector associated with a current vector that is calculated based on a current position of a first reference marker (e.g., internal reference marker 24) and a current position of a second reference marker (e.g., external reference marker 22), as described in more detail above. The second reference marker is depicted in at least one image of the set of images. In some embodiments, the viewing the representation of the instrument includes detecting a representation of a third reference marker. The third reference marker can be disposed on the instrument, similar to the instrument reference marker 18, described above.

Optionally, the method 450 includes generating the set of images. The set of images can be generated using any suitable imaging modality described herein. For example, the set of images can be generated using at least one of a 2D, 3D, or a 4D imaging modality (or imaging device). In some embodiments, for example, the set of images is generated using at least one of fluoroscopy, computed tomography, magnetic resonance imaging, positron emission tomography, ultrasound, or optical coherence tomography.

The method 450 includes adjusting a position of the instrument based on the viewing such that a portion of the instrument is at a location within the body of the patient, 454. For example, the adjusting can include moving the medical instrument 16 from a first position to a second position different than the first position. In some embodiments, the position of the medical instrument 16 is adjusted such that the medical instrument 16 is at a location within the patient's 10 body that is proximate to an opening formed in or by the target anatomy. In some embodiments, for example, the opening can be a puncture or an incision site formed in the target anatomy. The puncture or incision site, for example, may have been formed by the physician 14 using the medical instrument 16 while performing a medical procedure (e.g., a biopsy) in or proximate to the target anatomy. In another example, the opening can be a natural bodily opening formed by the body of the patient, such as due to genetics and/or disease.

The method 450 includes delivering a sealant via the instrument to the location within the body of the patient, 456. The sealant is configured to seal an opening in the body part. For example, the sealant can be configured to seal a puncture or incision site or a natural body opening, described above. In some embodiments, the sealant is configured to form a seal between a portion of the instrument and the body part defining the opening, as described above with respect to instrument 580. As described above, the sealant can include any suitable material, including, but not limited to thrombin, fibrinogen, a cyanocrylate, collagen, a cross-linker, an aldehyde, or a hydrogel.

In some embodiments, the method 450 optionally includes detecting a first pressure within a portion of the body of the patient proximate to the instrument at a first time and detecting a second pressure within a portion of the body of the patient proximate to the instrument at a second time later than the first time. The second pressure is at least a threshold value. The delivering the sealant is performed when the second pressure is detected. For example, referring to the use of instrument 500 in a lung biopsy procedure, at least a portion of the instrument 500 can be positioned within a lung of the patient. The first pressure can be a pressure associated with the lung being filled with an amount fluid (e.g., air, a bodily liquid). For example, the first pressure can be a pressure within the lung associated with exhalation by the patient. The second pressure can be a pressure associated with the lung being filled with a different amount of fluid. For example, the second pressure can be a pressure within the lung associated with inhalation by the patient. Each of the first pressure and the second pressure is detected by the sensor 526. In this manner, the physician can deliver the sealant upon detecting the second pressure, for example, when the patient's lung is inflated and/or filled with the fluid to a specified amount.

In some embodiments, the method 450 optionally includes detecting a first pressure within a portion of the body of the patient proximate to the instrument at its first position and detecting a second pressure within a portion of the body of the patient proximate to the instrument at its second position different than the first position. The second pressure is at least a threshold value, and the delivering is performed when the second pressure is detected. For example, in a lung biopsy procedure, the first pressure can detected within a lung of the patient when the instrument is disposed at a first position proximate to and/or within the lung. The second pressure can be, for example, a pressure at an area at the surface of the lung and/or exterior to the lung proximate to the instrument at its second position. In this manner, the spatial change in pressure from the first location within the lung to the second location at the surface of and/or exterior to the lung facilitates detection by the physician of where the instrument is positioned with respect to the lung. In other words, the physician can detect the first pressure representing a pressure associated with the first location inside of the lung. The physician can then move the instrument until the physician detects the second pressure representing a pressure associated with the second location outside of the lung. In this manner, the physician can detect when the instrument is moved outside of the lung (e.g., and is proximate to the lung surface) by detecting the change in pressure, and thus can deliver the sealant when the instrument is outside of the lung. Also in this manner, because the physician can detect the change in pressure as it occurs, the sealant can be delivered to the puncture site at which the instrument entered the lung.

In some embodiments, the delivering includes releasing a seal member from a delivery instrument and disposing the seal member on or proximate to a body part having cyclical movement. For example, in some embodiments, seal member 620 is moved to its expanded configuration and is then released from instrument 600. The seal member 620 can, for example, become disengaged from the delivery mechanism 612 after the adhesive 626 of the seal member 620 contacts the bodily tissue B. In another example, the seal member 620 is released from the delivery mechanism 612 when the delivery mechanism is moved to its second configuration. The protrusion 614, for example, can be configured to disengage the seal member 620 from the delivery mechanism 612.

In some embodiments, the delivering includes disposing at least a portion of the sealant on an interior surface of the body part. For example, in some embodiments, the sealant can be disposed on a surface of a substrate of a seal member (e.g., a patch). The seal member, including the sealant, can be delivered to (or disposed on) an interior surface of the lung, for example, using instrument 600. In use, the seal member is moved from its collapsed configuration (e.g., its first configuration) to its expanded configuration (e.g., its second configuration) while the distal end portion 605 of the instrument 600 is disposed within an interior cavity of the lung. The instrument 600 is then withdrawn from the lung of the patient. As the instrument 600 is withdrawn, the expanded seal member engages the interior surface of the lung. Because the seal member is expanded, it is not withdrawn with the instrument 600, and thus remains in the lung.

In some embodiments, the delivering includes exposing a coating disposed on an outer surface of a portion of the instrument to a bodily fluid. For example, the exposing the coating 588 can cause a physical stage change in the coating as described above with respect to instrument 580. In some embodiments, the coating 588 is placed in contact with the body part having cyclical movement (e.g., the target dynamic anatomy).

In some embodiments, the delivering includes moving a first shaft of the instrument with respect to a second shaft of the instrument to place an opening defined by the first shaft in fluid communication with an opening defined by the second shaft. For example, as described above with respect to instrument 500, the first shaft 502 defines the opening 506 and the second shaft defines the opening 518. The second shaft 512 can be rotated to align the openings 506, 518. In this manner, the opening 506 of the first shaft 502 is placed in fluid communication with the chamber 514 of the second shaft 512, and the sealant can be delivered.

In some embodiments, the delivering includes delivering a seal member including the sealant via a working channel of an instrument, for example, via the lumen 606 of the instrument 600. In some embodiments, the delivering includes delivering a seal member that is wrapped about a portion of the delivery instrument. For example, in some embodiments, at least a portion of the seal member is wrapped about a distal end portion of the delivery instrument. To deliver the seal member, and thus a sealant disposed on the seal member, the portion of the delivery instrument including the seal member can be twisted and/or twirled to release and/or expand the seal member. In some embodiments, the physician maintains the position of the delivery instrument, and thus the seal member, to allow an adhesive disposed on the seal member to adhere to the bodily tissue. The delivery instrument can then be withdrawn from the body of the patient, leaving the seal member within the body of the patient.

In some embodiments, the delivering includes inserting a seal member including the sealant and that is disposed about an outer surface of an elongate shaft into, through, beyond, or proximate to the target anatomy. The elongate shaft is withdrawn from the anatomy and, because the seal member is loosely coupled to the outer surface of the elongate shaft, the seal member is released from the elongate shaft. In some embodiments, a portion of the seal member is withdrawn with the elongate shaft such that the seal member is disposed within and/or occludes the puncture opening.

In some embodiments, the delivering includes delivering a seal member including the sealant with an instrument having a plurality of shafts. The seal member is coupled to the instrument such that, upon a rotation (or twisting) and/or translation (or pushing or pulling) of one shaft with respect to another shaft, a flap portion of the seal member is expanded. In use, the instrument is used to position the seal member proximate to the desired location within the body of the patient. The physician then moves the one shaft in at least one of a rotational or a translational movement with respect to the second shaft until the flap portion of the seal member is expanded (or exposed). The physician then engages the bodily tissue with the expanded seal member to adhere at least a portion of the seal member to the bodily tissue. As the instrument is withdrawn from the body of the patient, the seal member remains adhered to the bodily tissue. When the instrument is fully withdrawn from the body of the patient, at least one flap one the flap portion of the seal member overlap to seal the puncture opening.

In some embodiments, the method 450 also includes applying an activation agent to or proximate to the sealant. For example, in some embodiments, the activation agent is an energy source. The energy source can be, for example, a light source, a heat source, or the like. Referring to instrument 500, the energy source can be disposed within the lumen 516 of the second shaft 512 such that energy from the energy source can reach (or access) the sealant within the body of the patient. In some embodiments, the activation agent is a chemical, a solution, a polymer, or the like configured to initiate a phase change in the sealant, and thus activate the sealant.

Although various embodiments have been described as having particular features and/or combinations of components, other embodiments are possible having a combination of any features and/or components from any embodiment, as discussed above.

What is claimed is:

1. An apparatus for delivering a sealant to a patient's lung tissue, comprising:
   a first shaft defining a lumen, a tapered distal tip configured to penetrate a bodily tissue proximate of the patient's lung, and an opening on the tapered distal tip in communication with the lumen of the first shaft, at least a portion of the first shaft disposable within a body of a patient; and
   a second shaft defining a chamber, the second shaft having a second shaft tapered distal tip, and an opening on the second shaft tapered distal tip in communication with the chamber of the second shaft, the chamber of the second shaft configured to receive a liquid fibrin sealant, the liquid fibrin sealant being transitional from a liquid state to a solid state upon exposure to bodily fluids of the patient's lung tissue,
   the second shaft configured to be movably received within the lumen of the first shaft, the second shaft having a first position in which the opening of the second shaft is fluidically isolated from the opening of the first shaft and a second position in which the opening of the second shaft is in fluid communication with the opening of the first shaft, the opening of the first shaft and the opening of the second shaft defining a flow passageway for the sealant when the second shaft is in its second position, wherein the flow passageway is configured to permit movement of the liquid fibrin sealant from the chamber of the second shaft to a location exterior to the first shaft;
   thereby preventing transition of the liquid fibrin sealant by the patient's lung tissue until the flow passageway is uncovered by motion of the second shaft into the second position.

2. The apparatus of claim 1, further comprising a plunger disposed within the chamber of the second shaft, the plunger configured to facilitate delivery of the sealant to the body of the patient.

3. The apparatus of claim 1, wherein at least one of the first shaft or the second shaft includes a first reference marker, the first reference marker viewable by an imaging device that is exterior the body of the patient when the first reference marker is disposed within the body of the patient.

4. The apparatus of claim 1, wherein the second shaft is movable with respect to the first shaft in at least one of a rotational direction or a translational direction.

5. The apparatus of claim 1, wherein the first shaft includes a coating disposed on an outer surface of at least a portion of the first shaft, the coating configured to form a seal between the portion of the first shaft and a portion of the body of the patient in contact with the outer surface of the portion of the first shaft.

6. The apparatus of claim 1, wherein the sealant includes at least one of thrombin, fibrinogen, a cyanoacrylate, collagen, a cross-linker, an aldehyde, or a hydrogel.

7. The apparatus of claim 1, further comprising: a sensor coupled to a distal end portion of at least one of the first shaft or the second shaft, the sensor configured to sense a pressure within a portion of the body of the patient in which the sensor is disposed.

8. The apparatus of claim 3, comprising a second reference marker;
   the first shaft, the second shaft and the first reference marker defining a medical instrument;
   the imaging device configured to display a representation of the medical instrument, the representation being superimposed on an image of a plurality of images associated with a match dataset vector (MDV), the MDV being a dataset vector most similar to a current position of the first reference marker and a current position of the second reference marker, the second reference marker being depicted in at least one image of the plurality of images.

9. The apparatus of claim 1, wherein the opening on the tapered distal tip of the first shaft is in fluid communication with the opening on the second shaft tapered distal tip when the second shaft is in the second position.

* * * * *